US011957401B2

(12) United States Patent
Batchelor et al.

(10) Patent No.: US 11,957,401 B2
(45) Date of Patent: Apr. 16, 2024

(54) ELECTROSURGICAL INSTRUMENT

(71) Applicant: GYRUS ACMI, INC., Southborough, MA (US)

(72) Inventors: Kester J. Batchelor, Mound, MN (US); Riyad Moe, Waunakee, WI (US)

(73) Assignee: Gyrus ACMI, Inc., Westborough, MA (US)

( * ) Notice: Subject to any disclaimer, the term of this patent is extended or adjusted under 35 U.S.C. 154(b) by 900 days.

(21) Appl. No.: 16/385,013

(22) Filed: Apr. 16, 2019

(65) Prior Publication Data

US 2019/0239942 A1 Aug. 8, 2019

Related U.S. Application Data

(63) Continuation of application No. 14/178,411, filed on Feb. 12, 2014, now Pat. No. 10,292,757.

(60) Provisional application No. 61/902,933, filed on Nov. 12, 2013, provisional application No. 61/787,731, filed on Mar. 15, 2013.

(51) Int. Cl.
*A61B 18/12* (2006.01)
*A61B 18/14* (2006.01)
*A61B 18/00* (2006.01)

(52) U.S. Cl.
CPC ...... *A61B 18/1442* (2013.01); *A61B 18/1445* (2013.01); *A61B 2018/00089* (2013.01); *A61B 2018/00607* (2013.01); *A61B 2018/1253* (2013.01); *A61B 2018/126* (2013.01); *A61B 2018/1467* (2013.01)

(58) Field of Classification Search
CPC ............ A61B 18/1442; A61B 18/1445; A61B 2018/126
See application file for complete search history.

(56) References Cited

U.S. PATENT DOCUMENTS

| | | |
|---|---|---|
| 1,198,958 A | 9/1916 | Risely |
| 1,530,952 A | 3/1925 | Lawton |
| 2,042,985 A | 6/1936 | Gardella |
| 2,214,984 A | 9/1940 | Buchmann |
| 2,381,084 A | 8/1945 | Slad |
| 2,575,652 A | 11/1951 | Bovee |
| 2,894,424 A | 7/1959 | Vaughan |
| 3,399,583 A | 9/1968 | Hall |
| 3,417,752 A | 12/1968 | Butler |

(Continued)

FOREIGN PATENT DOCUMENTS

| | | |
|---|---|---|
| AU | 2014235755 A1 | 7/2015 |
| AU | 2015205939 A1 | 8/2015 |

(Continued)

OTHER PUBLICATIONS

Potentially related U.S. Appl. No. 14/589,482, filed Jan. 5, 2015 published as 2015/0148798 dated May 28, 2015.

(Continued)

*Primary Examiner* — Daniel W Fowler
(74) *Attorney, Agent, or Firm* — Schwegman Lundberg & Woessner, P.A.

(57) ABSTRACT

An electrosurgical instrument comprising a first arm carrying at least a first and optionally a second and third electrode, and a second arm opposing the first arm, the second arm carrying one of a nonconductor element or one or more conductive elements.

22 Claims, 15 Drawing Sheets

(56) References Cited

U.S. PATENT DOCUMENTS

| | | |
|---|---|---|
| 3,465,621 A | 9/1969 | Ladd |
| 3,576,072 A | 4/1971 | Foster |
| 3,643,663 A | 2/1972 | Sutter |
| 3,685,518 A | 8/1972 | Beuerle et al. |
| 3,699,632 A | 10/1972 | Anhalt |
| 3,817,078 A | 6/1974 | Reed et al. |
| 3,818,784 A | 6/1974 | McClure |
| 3,913,586 A | 10/1975 | Baumgarten |
| 4,041,952 A | 8/1977 | Morrison, Jr. et al. |
| 4,154,226 A | 5/1979 | Hennig et al. |
| 4,171,700 A | 10/1979 | Farin |
| 4,202,337 A | 5/1980 | Hren et al. |
| 4,318,313 A | 3/1982 | Tartaglia |
| 4,375,218 A | 3/1983 | DiGeronimo |
| 4,407,069 A | 10/1983 | Conners |
| 4,418,692 A | 12/1983 | Guay |
| 4,443,935 A | 4/1984 | Zamba et al. |
| 4,463,759 A | 7/1984 | Garito et al. |
| 4,492,231 A | 1/1985 | Auth |
| 4,492,832 A | 1/1985 | Taylor |
| 4,494,543 A | 1/1985 | Hart |
| 4,504,707 A | 3/1985 | Ochiai |
| 4,524,648 A | 6/1985 | Chung |
| 4,552,143 A | 11/1985 | Lottick |
| 4,655,215 A | 4/1987 | Pike |
| 4,669,470 A | 6/1987 | Brandfield |
| 4,686,980 A | 8/1987 | Williams et al. |
| 4,688,569 A | 8/1987 | Rabinowitz |
| 4,713,885 A | 12/1987 | Keklak et al. |
| 4,757,612 A | 7/1988 | Peyrot |
| 4,784,136 A | 11/1988 | Klein |
| 4,860,745 A | 8/1989 | Farin et al. |
| 4,896,661 A | 1/1990 | Bogert et al. |
| 4,935,027 A | 6/1990 | Yoon |
| 5,021,616 A | 6/1991 | Hardt |
| 5,035,695 A | 7/1991 | Weber, Jr. et al. |
| 5,071,426 A | 12/1991 | Dolgin et al. |
| 5,104,397 A | 4/1992 | Vasconcelos et al. |
| 5,108,392 A | 4/1992 | Spingler |
| 5,147,378 A | 9/1992 | Markham |
| 5,176,702 A | 1/1993 | Bales et al. |
| 5,190,541 A | 3/1993 | Abele et al. |
| 5,196,009 A | 3/1993 | Kirwan, Jr. |
| 5,207,691 A | 5/1993 | Nardella |
| 5,207,696 A | 5/1993 | Matwijcow |
| 5,208,983 A | 5/1993 | Masse |
| 5,226,904 A | 7/1993 | Gentelia et al. |
| 5,281,216 A | 1/1994 | Klicek |
| 5,290,286 A | 3/1994 | Parins |
| 5,293,878 A | 3/1994 | Bales et al. |
| 5,318,589 A | 6/1994 | Lichtman |
| 5,342,359 A | 8/1994 | Rydell |
| 5,370,659 A | 12/1994 | Sakashita |
| 5,401,272 A * | 3/1995 | Perkins ............ A61B 18/24 606/50 |
| 5,403,312 A | 4/1995 | Yates et al. |
| 5,413,575 A | 5/1995 | Haenggi |
| 5,423,814 A | 6/1995 | Zhu et al. |
| 5,425,743 A | 6/1995 | Nicholas |
| 5,440,813 A | 8/1995 | Roskam |
| 5,441,498 A | 8/1995 | Perkins |
| 5,443,463 A | 8/1995 | Stern |
| 5,456,695 A | 10/1995 | Dellamagne |
| 5,458,598 A | 10/1995 | Fienberg et al. |
| 5,472,442 A | 12/1995 | Klicek |
| 5,483,952 A | 1/1996 | Aranyi |
| 5,484,435 A | 1/1996 | Fleenor et al. |
| 5,499,998 A | 3/1996 | Meade |
| 5,531,744 A | 7/1996 | Nardella et al. |
| 5,540,685 A | 7/1996 | Parins et al. |
| 5,562,503 A | 10/1996 | Ellman et al. |
| 5,573,424 A | 11/1996 | Poppe |
| 5,626,577 A | 5/1997 | Harris |
| 5,658,281 A * | 8/1997 | Heard ............ A61B 18/1445 606/41 |
| 5,674,220 A | 10/1997 | Fox |
| 5,693,052 A | 12/1997 | Weaver |
| 5,702,390 A | 12/1997 | Austin et al. |
| 5,709,680 A | 1/1998 | Yates et al. |
| 5,735,849 A | 4/1998 | Baden et al. |
| 5,779,701 A | 7/1998 | McBrayer et al. |
| 5,810,805 A | 9/1998 | Sutcu et al. |
| 5,827,281 A | 10/1998 | Levin |
| 5,884,954 A | 3/1999 | Trozera |
| 5,891,140 A | 4/1999 | Ginn et al. |
| 5,902,300 A * | 5/1999 | Hahnen ............ A61B 18/1485 606/49 |
| 5,902,301 A | 5/1999 | Dlig |
| 5,922,001 A | 7/1999 | Yoon |
| 5,951,545 A | 9/1999 | Schilling et al. |
| 6,024,741 A | 2/2000 | Williamson, IV et al. |
| 6,030,384 A | 2/2000 | Nezhat |
| 6,039,734 A | 3/2000 | Goble |
| 6,050,996 A | 4/2000 | Schmaltz et al. |
| 6,053,908 A | 4/2000 | Crainich et al. |
| 6,074,386 A | 6/2000 | Goble et al. |
| 6,099,550 A | 8/2000 | Yoon |
| 6,102,909 A | 8/2000 | Chen et al. |
| 6,110,171 A | 8/2000 | Rydell |
| 6,113,596 A | 9/2000 | Hooven et al. |
| 6,117,158 A | 9/2000 | Measamer et al. |
| 6,117,169 A | 9/2000 | Moe |
| 6,152,923 A | 11/2000 | Ryan |
| 6,174,309 B1 | 1/2001 | Wrublewski et al. |
| 6,190,386 B1 | 2/2001 | Rydell |
| 6,270,497 B1 | 8/2001 | Sekino et al. |
| 6,273,887 B1 | 8/2001 | Yamauchi |
| 6,325,795 B1 | 12/2001 | Lidemann et al. |
| 6,355,032 B1 | 3/2002 | Hovda et al. |
| 6,358,268 B1 | 3/2002 | Hunt et al. |
| 6,402,747 B1 | 6/2002 | Lindemann et al. |
| 6,428,538 B1 | 8/2002 | Blewett et al. |
| 6,458,128 B1 | 10/2002 | Schulze |
| 6,464,698 B1 | 10/2002 | Falwell |
| 6,464,704 B2 | 10/2002 | Schmaltz et al. |
| 6,486,419 B2 | 11/2002 | Horiguchi et al. |
| 6,494,886 B1 | 12/2002 | Wilk et al. |
| 6,514,252 B2 | 2/2003 | Nezhat et al. |
| 6,551,313 B1 | 4/2003 | Levin |
| 6,585,735 B1 | 7/2003 | Frazier et al. |
| 6,619,038 B2 | 9/2003 | Takada et al. |
| 6,623,499 B1 | 9/2003 | Andreini et al. |
| 6,641,595 B1 | 11/2003 | Moran et al. |
| 6,652,514 B1 | 11/2003 | Ellman et al. |
| 6,679,882 B1 | 1/2004 | Kornerup |
| 6,689,130 B2 | 2/2004 | Arai et al. |
| 6,695,840 B2 | 2/2004 | Schulze |
| 6,726,686 B2 | 4/2004 | Buysse et al. |
| 6,749,610 B2 | 6/2004 | Kirwan, Jr. et al. |
| 6,752,767 B2 | 6/2004 | Turovskiy et al. |
| 6,773,434 B2 | 8/2004 | Ciarrocca |
| 6,808,525 B2 | 10/2004 | Latterell et al. |
| 6,827,717 B2 | 12/2004 | Brommersma et al. |
| 6,860,882 B2 | 3/2005 | Battles et al. |
| 6,926,716 B2 | 8/2005 | Baker et al. |
| 6,942,662 B2 | 9/2005 | Goble et al. |
| 7,083,613 B2 | 8/2006 | Treat |
| 7,094,231 B1 | 8/2006 | Ellman et al. |
| 7,108,694 B2 | 9/2006 | Miura et al. |
| 7,112,199 B2 | 9/2006 | Cosmescu |
| 7,147,637 B2 | 12/2006 | Goble |
| 7,147,638 B2 | 12/2006 | Chapman et al. |
| 7,150,749 B2 | 12/2006 | Dyeus et al. |
| 7,156,846 B2 | 1/2007 | Dycus et al. |
| 7,232,440 B2 | 6/2007 | Dumbauld et al. |
| 7,244,257 B2 | 7/2007 | Podhajsky et al. |
| 7,252,667 B2 | 8/2007 | Moses et al. |
| 7,344,536 B1 | 3/2008 | Lunsford et al. |
| 7,367,976 B2 | 5/2008 | Lawes et al. |
| 7,377,902 B2 | 5/2008 | Burbank |
| 7,473,253 B2 | 1/2009 | Dycus |
| 7,481,810 B2 | 1/2009 | Dumbauld et al. |
| 7,503,917 B2 | 3/2009 | Sartor et al. |
| 7,604,635 B2 | 10/2009 | McClurken et al. |

(56) References Cited

U.S. PATENT DOCUMENTS

| | | |
|---|---|---|
| 7,625,391 B2 | 12/2009 | Kebel et al. |
| 7,651,494 B2 | 1/2010 | Mcclurken et al. |
| 7,674,261 B2 | 3/2010 | Garito et al. |
| 7,686,827 B2 | 3/2010 | Hushka |
| 7,722,607 B2 | 5/2010 | Dumbauld et al. |
| 7,753,909 B2 | 7/2010 | Chapman et al. |
| 7,758,577 B2 | 7/2010 | Nobis et al. |
| 7,789,878 B2 | 9/2010 | Dumbauld et al. |
| 7,879,035 B2 | 2/2011 | Garrison et al. |
| 7,896,875 B2 | 3/2011 | Heim et al. |
| 7,909,820 B2 | 3/2011 | Lipson et al. |
| 7,922,718 B2 | 4/2011 | Moses et al. |
| 7,931,649 B2 | 4/2011 | Couture |
| 7,931,668 B2 | 4/2011 | Sloat |
| 7,938,469 B2 | 5/2011 | Ait-Mani |
| 7,942,872 B2 | 5/2011 | Ein-Gal |
| 7,955,331 B2 | 6/2011 | Truckai et al. |
| 7,998,140 B2 | 8/2011 | McClurken et al. |
| 8,062,292 B1 | 11/2011 | Slater |
| 8,100,894 B2 | 1/2012 | Mucko et al. |
| 8,162,940 B2 | 4/2012 | Johnson et al. |
| 8,216,231 B2 | 7/2012 | Behl et al. |
| 8,226,649 B2 | 7/2012 | Falkenstein et al. |
| 8,246,094 B2 | 8/2012 | Long et al. |
| 8,251,989 B1 | 8/2012 | Newton et al. |
| 8,257,352 B2 | 9/2012 | Lawes et al. |
| 8,262,655 B2 | 9/2012 | Ghabrial et al. |
| 8,267,935 B2 | 9/2012 | Couture et al. |
| 8,287,534 B2 | 10/2012 | Balog |
| 8,328,170 B2 | 12/2012 | Wasinger |
| 8,361,065 B2 | 1/2013 | West et al. |
| 8,361,072 B2 | 1/2013 | Dumbauld et al. |
| 8,485,413 B2 | 7/2013 | Scheib et al. |
| 8,491,626 B2 | 7/2013 | Roy et al. |
| 8,496,603 B2 | 7/2013 | Mamourian |
| 8,568,411 B2 | 10/2013 | Falkenstein et al. |
| 8,628,529 B2 | 1/2014 | Aldridge |
| 8,632,553 B2 | 1/2014 | Sakamoto et al. |
| 8,702,691 B2 | 4/2014 | Weber et al. |
| 8,702,700 B2 | 4/2014 | Maeda et al. |
| 8,882,756 B2 | 11/2014 | Greeley et al. |
| 8,939,972 B2 | 1/2015 | Twomey |
| 9,023,035 B2 | 5/2015 | Allen et al. |
| 9,204,879 B2 | 12/2015 | Shelton |
| 9,320,563 B2 | 4/2016 | Brustad et al. |
| 9,326,810 B2 | 5/2016 | Shilev et al. |
| 9,358,065 B2 | 6/2016 | Ladtkow et al. |
| 9,439,665 B2 | 9/2016 | Marczyk et al. |
| 9,445,863 B2 | 9/2016 | Batchelor et al. |
| 9,452,009 B2 | 9/2016 | Batchelor et al. |
| 9,452,011 B2 | 9/2016 | Batchelor et al. |
| 9,668,805 B2 | 6/2017 | Batchelor et al. |
| 9,763,730 B2 | 9/2017 | Batchelor et al. |
| 9,901,388 B2 | 2/2018 | Batchelor et al. |
| 9,901,389 B2 | 2/2018 | Batchelor |
| 10,085,793 B2 | 10/2018 | Batchelor |
| 10,271,895 B2 | 4/2019 | Batchelor et al. |
| 10,292,757 B2 | 5/2019 | Batchelor et al. |
| 10,828,087 B2 | 11/2020 | Batchelor et al. |
| 10,893,900 B2 | 1/2021 | Windgassen et al. |
| 11,224,477 B2 | 1/2022 | Windgassen et al. |
| 11,744,634 B2 | 9/2023 | Batchelor |
| 11,779,384 B2 | 10/2023 | Batchelor et al. |
| 2002/0106609 A1 | 8/2002 | Palermo et al. |
| 2002/0107517 A1 | 8/2002 | Witt |
| 2002/0115997 A1 | 8/2002 | Truckai et al. |
| 2003/0014850 A1 | 1/2003 | Banitt et al. |
| 2003/0018329 A1 | 1/2003 | Hooven |
| 2003/0144652 A1 | 1/2003 | Baker et al. |
| 2003/0050633 A1 | 3/2003 | Ellman |
| 2003/0097126 A1 | 5/2003 | Woloszko et al. |
| 2003/0106609 A1 | 6/2003 | Leoncavallo |
| 2003/0109876 A1 | 6/2003 | Yamauchi |
| 2003/0114850 A1 | 6/2003 | McClurken et al. |
| 2003/0144605 A1 | 7/2003 | Burbank et al. |
| 2003/0181904 A1 | 9/2003 | Levine et al. |
| 2004/0030330 A1 | 2/2004 | Brassell et al. |
| 2004/0082946 A1 | 4/2004 | Malis |
| 2004/0097117 A1 | 5/2004 | Gonnering |
| 2004/0097912 A1 | 5/2004 | Gonnering |
| 2005/0065510 A1 | 3/2005 | Carmel et al. |
| 2005/0113824 A1 | 5/2005 | Sartor |
| 2005/0113825 A1 | 5/2005 | Cosmescu |
| 2005/0113827 A1 | 5/2005 | Dumbauld et al. |
| 2005/0159745 A1 | 7/2005 | Truckai et al. |
| 2005/0187512 A1 | 8/2005 | Isola et al. |
| 2005/0216019 A1 | 9/2005 | Eckman |
| 2006/0004355 A1 | 1/2006 | Anders et al. |
| 2006/0084973 A1 | 4/2006 | Hushka |
| 2006/0167450 A1 | 7/2006 | Johnson et al. |
| 2006/0190035 A1 | 8/2006 | Hushka et al. |
| 2006/0217701 A1 | 9/2006 | Young et al. |
| 2007/0049922 A1 | 3/2007 | Rontal |
| 2007/0078458 A1 | 4/2007 | Dambauld et al. |
| 2007/0093857 A1 | 4/2007 | Campbell |
| 2007/0106295 A1 | 5/2007 | Garrison et al. |
| 2007/0123855 A1 | 5/2007 | Morley et al. |
| 2007/0129716 A1 | 6/2007 | Daw |
| 2007/0179491 A1 | 8/2007 | Kratoska et al. |
| 2008/0033428 A1 | 2/2008 | Artale et al. |
| 2008/0077129 A1 | 3/2008 | Van Wyk et al. |
| 2008/0147092 A1 | 6/2008 | Rogge et al. |
| 2008/0154300 A1 | 6/2008 | Jabbour |
| 2008/0236860 A1 | 10/2008 | Howe |
| 2008/0287948 A1 | 11/2008 | Newton et al. |
| 2009/0030414 A1 | 1/2009 | Bayat |
| 2009/0062786 A1 | 3/2009 | Garito et al. |
| 2009/0062792 A1 | 3/2009 | Vakharia et al. |
| 2009/0062830 A1 | 3/2009 | Hiraoka |
| 2009/0082768 A1 | 3/2009 | Bacher et al. |
| 2009/0093804 A1 | 4/2009 | Newton |
| 2009/0138003 A1 | 5/2009 | DeVille et al. |
| 2009/0138013 A1 | 5/2009 | Thorne et al. |
| 2009/0171147 A1 | 7/2009 | Lee et al. |
| 2009/0192509 A1 | 7/2009 | Curtis |
| 2009/0248002 A1 | 10/2009 | Takashino et al. |
| 2010/0042096 A1 | 2/2010 | Ellman |
| 2010/0069940 A1 | 3/2010 | Miller et al. |
| 2010/0087814 A1 | 4/2010 | Desinger et al. |
| 2010/0137854 A1 | 6/2010 | Hosier |
| 2010/0179545 A1 | 7/2010 | Twomey et al. |
| 2010/0228249 A1 | 9/2010 | Mohr |
| 2010/0233913 A1 | 9/2010 | Kuhne |
| 2010/0241119 A1 | 9/2010 | Bayat |
| 2010/0298865 A1 | 11/2010 | Aufaure et al. |
| 2011/0028964 A1* | 2/2011 | Edwards ............ A61B 18/1442 606/48 |
| 2011/0045680 A1 | 2/2011 | Beller |
| 2011/0054462 A1 | 3/2011 | Ellman |
| 2011/0054467 A1 | 3/2011 | Mueller et al. |
| 2011/0071525 A1 | 3/2011 | Dumbauld et al. |
| 2011/0077648 A1 | 3/2011 | Lee et al. |
| 2011/0098733 A1 | 4/2011 | Huynh |
| 2011/0112530 A1 | 5/2011 | Keller |
| 2011/0178515 A1 | 7/2011 | Bloom et al. |
| 2011/0224669 A1 | 9/2011 | Podany |
| 2011/0230875 A1 | 9/2011 | Walberg et al. |
| 2011/0251613 A1 | 10/2011 | Guerra et al. |
| 2011/0290854 A1 | 12/2011 | Timm et al. |
| 2011/0319892 A1 | 12/2011 | Blomeyer |
| 2012/0022530 A1 | 1/2012 | Woodruff et al. |
| 2012/0078292 A1 | 3/2012 | Banju |
| 2012/0095460 A1 | 4/2012 | Rooks et al. |
| 2012/0101501 A1 | 4/2012 | Nishimura et al. |
| 2012/0107517 A1 | 5/2012 | Shibata et al. |
| 2012/0123405 A1 | 5/2012 | Moua et al. |
| 2012/0123409 A1 | 5/2012 | Tani et al. |
| 2012/0136347 A1 | 5/2012 | Brustad et al. |
| 2012/0150165 A1 | 6/2012 | Conley |
| 2012/0202388 A1 | 8/2012 | Selig |
| 2012/0232553 A1 | 9/2012 | Bloom et al. |
| 2012/0253229 A1 | 10/2012 | Cage |
| 2012/0310229 A1 | 12/2012 | Gregg |
| 2013/0023874 A1 | 1/2013 | Lawes et al. |

(56) References Cited

U.S. PATENT DOCUMENTS

| | | |
|---|---|---|
| 2013/0066317 A1 | 3/2013 | Evans et al. |
| 2013/0079762 A1 | 3/2013 | Twomey et al. |
| 2013/0079764 A1 | 3/2013 | Schaller et al. |
| 2013/0138096 A1 | 5/2013 | Benn |
| 2013/0178852 A1 | 7/2013 | Allen, IV et al. |
| 2013/0237982 A1 | 9/2013 | Rencher et al. |
| 2013/0296846 A1 | 11/2013 | Canady et al. |
| 2014/0100569 A1 | 4/2014 | Lawes et al. |
| 2014/0236202 A1 | 8/2014 | Palmer et al. |
| 2014/0276772 A1 | 9/2014 | Batchelor et al. |
| 2014/0276785 A1 | 9/2014 | Batchelor et al. |
| 2014/0276786 A1 | 9/2014 | Batchelor |
| 2014/0276794 A1 | 9/2014 | Batchelor et al. |
| 2014/0276795 A1 | 9/2014 | Batchelor et al. |
| 2014/0276796 A1 | 9/2014 | Batchelor et al. |
| 2014/0276797 A1 | 9/2014 | Batchelor et al. |
| 2014/0276798 A1 | 9/2014 | Batchelor et al. |
| 2014/0276799 A1 | 9/2014 | Batchelor et al. |
| 2014/0276800 A1 | 9/2014 | Batchelor et al. |
| 2014/0276804 A1 | 9/2014 | Batchelor |
| 2015/0119885 A1 | 4/2015 | Windgassen et al. |
| 2015/0148798 A1 | 5/2015 | Windgassen et al. |
| 2015/0320485 A1 | 11/2015 | Batchelor et al. |
| 2016/0051273 A1 | 2/2016 | Batchelor et al. |
| 2016/0051275 A1 | 2/2016 | Batchelor et al. |
| 2016/0051314 A1 | 2/2016 | Batchelor et al. |
| 2016/0346033 A1 | 12/2016 | Batchelor et al. |
| 2017/0319263 A1 | 11/2017 | Batchelor et al. |
| 2018/0333196 A1 | 11/2018 | Batchelor |
| 2019/0247110 A1 | 8/2019 | Batchelor et al. |

FOREIGN PATENT DOCUMENTS

| | | |
|---|---|---|
| AU | 2015207838 A1 | 8/2015 |
| AU | 2015205939 B2 | 3/2017 |
| AU | 2015207838 B2 | 3/2017 |
| AU | 2014235755 B2 | 11/2018 |
| BR | 122015018776 A2 | 8/2019 |
| BR | 122015018777 A2 | 8/2019 |
| CN | 1149519 A | 5/1997 |
| CN | 1889893 A | 1/2007 |
| CN | 1929794 A | 3/2007 |
| CN | 101460110 A | 6/2009 |
| CN | 101902979 A | 12/2010 |
| CN | 102068307 A | 5/2011 |
| CN | 102164556 A | 8/2011 |
| CN | 102525639 A | 7/2012 |
| CN | 102836006 A | 12/2012 |
| CN | 104994802 A | 10/2015 |
| CN | 105025833 A | 11/2015 |
| CN | 105142556 A | 12/2015 |
| CN | 105142557 A | 12/2015 |
| CN | 105163683 A | 12/2015 |
| CN | 105208955 A | 12/2015 |
| CN | 105208956 A | 12/2015 |
| CN | 105246424 A | 1/2016 |
| CN | 105246425 A | 1/2016 |
| CN | 105286992 A | 2/2016 |
| CN | 105380711 A | 3/2016 |
| CN | 105451678 A | 3/2016 |
| CN | 104994802 B | 9/2017 |
| CN | 105286992 B | 10/2017 |
| CN | 105025833 B | 11/2017 |
| CN | 105208956 B | 11/2017 |
| CN | 105380711 B | 1/2018 |
| CN | 105246424 B | 2/2018 |
| CN | 105246425 B | 3/2018 |
| CN | 108078625 A | 5/2018 |
| CN | 105163683 B | 6/2018 |
| CN | 105142557 B | 7/2018 |
| CN | 105208955 B | 11/2018 |
| CN | 105142556 B | 1/2019 |
| CN | 105451678 B | 7/2019 |
| CN | 108078625 B | 11/2020 |
| EP | 0392548 A1 | 10/1994 |
| EP | 1089664 | 4/2001 |
| EP | 1411847 A4 | 1/2005 |
| EP | 1530952 | 5/2005 |
| EP | 1769765 A1 | 4/2007 |
| EP | 1530952 A1 | 7/2007 |
| EP | 1810629 | 7/2007 |
| EP | 1810629 A1 | 7/2007 |
| EP | 1977706 | 10/2008 |
| EP | 1977706 A1 | 10/2008 |
| EP | 2403422 | 1/2012 |
| EP | 2928402 A1 | 10/2015 |
| EP | 2945557 A1 | 11/2015 |
| EP | 2967718 A1 | 1/2016 |
| EP | 2967719 A1 | 1/2016 |
| EP | 2967720 A1 | 1/2016 |
| EP | 2967724 A1 | 1/2016 |
| EP | 2967732 A1 | 1/2016 |
| EP | 2967735 A1 | 1/2016 |
| EP | 2967739 A1 | 1/2016 |
| EP | 2967741 A1 | 1/2016 |
| EP | 2974682 A1 | 1/2016 |
| EP | 2974684 A1 | 1/2016 |
| EP | 2945557 B1 | 1/2017 |
| EP | 2967718 B1 | 4/2017 |
| EP | 3158963 A1 | 4/2017 |
| EP | 2928402 B1 | 5/2017 |
| EP | 2967720 B1 | 5/2017 |
| EP | 2967719 B1 | 7/2017 |
| EP | 2974682 B1 | 8/2017 |
| EP | 2974684 B1 | 8/2017 |
| EP | 3210560 A1 | 8/2017 |
| EP | 2967732 B1 | 11/2017 |
| EP | 296772481 | 12/2017 |
| EP | 2967741 B1 | 2/2018 |
| EP | 3308731 A1 | 4/2018 |
| EP | 2967739 B1 | 5/2018 |
| EP | 2967735 B1 | 8/2018 |
| EP | 3427682 A1 | 1/2019 |
| EP | 3210560 B1 | 7/2019 |
| EP | 3308731 B1 | 10/2019 |
| EP | 3158963 B1 | 5/2020 |
| IN | 4353CHENP2015 A | 7/2016 |
| IN | 4990CHENP2015 A | 7/2016 |
| IN | 4991CHENP2015 A | 7/2016 |
| JP | 58193907 U | 12/1983 |
| JP | H08322847 A | 12/1996 |
| JP | H09503423 A | 4/1997 |
| JP | H09122140 A | 5/1997 |
| JP | H10-199 | 1/1998 |
| JP | H1057390 A | 3/1998 |
| JP | H10-137259 A | 5/1998 |
| JP | H10-504485 A | 5/1998 |
| JP | H10137259 A | 5/1998 |
| JP | 2000070280 A | 3/2000 |
| JP | 2000102545 A | 4/2000 |
| JP | 2001170070 A | 6/2001 |
| JP | 200278717 A | 3/2002 |
| JP | 2002528166 A | 9/2002 |
| JP | 2003210483 A | 7/2003 |
| JP | 2004508875 A | 3/2004 |
| JP | 2004147724 A | 5/2004 |
| JP | 2005144192 A | 6/2005 |
| JP | 2005518864 A | 6/2005 |
| JP | 2005521465 A | 7/2005 |
| JP | 2005538748 A | 12/2005 |
| JP | 2006116320 A | 5/2006 |
| JP | 2008-18226 | 1/2008 |
| JP | 2008018226 A | 1/2008 |
| JP | 2008119465 A | 5/2008 |
| JP | 2009182479 A | 8/2009 |
| JP | 2009247893 A | 10/2009 |
| JP | 2009297503 A | 12/2009 |
| JP | 2011506008 A | 3/2011 |
| JP | 2011212449 A | 10/2011 |
| JP | 2012152561 A | 8/2012 |
| JP | 2012517869 A | 8/2012 |
| JP | 2012518490 A | 8/2012 |
| JP | 2013502248 A | 1/2013 |
| JP | 2016047264 A | 4/2016 |

(56) References Cited

FOREIGN PATENT DOCUMENTS

| | | | |
|---|---|---|---|
| JP | 2016510633 A | 4/2016 | |
| JP | 2016510634 A | 4/2016 | |
| JP | 2016510635 A | 4/2016 | |
| JP | 2016510636 A | 4/2016 | |
| JP | 2016512079 A | 4/2016 | |
| JP | 2016512081 A | 4/2016 | |
| JP | 2016512720 A | 5/2016 | |
| JP | 2016513539 A | 5/2016 | |
| JP | 2016515864 A | 6/2016 | |
| JP | 2016516482 A | 6/2016 | |
| JP | 2016185321 A | 10/2016 | |
| JP | 2017038982 A | 2/2017 | |
| JP | 6109908 B2 | 3/2017 | |
| JP | 6129400 B2 | 4/2017 | |
| JP | 614150682 | 5/2017 | |
| JP | 6153654 B2 | 6/2017 | |
| JP | 6161780 B2 | 6/2017 | |
| JP | 6193469 B2 | 8/2017 | |
| JP | 6216031 B2 | 9/2017 | |
| JP | 6273346 B2 | 1/2018 | |
| JP | 6275813 B2 | 1/2018 | |
| JP | 6386010 B2 | 8/2018 | |
| JP | 2018140222 A | 9/2018 | |
| JP | 6440677 B2 | 11/2018 | |
| WO | 96/005776 A1 | 2/1996 | |
| WO | 9966850 | 12/1999 | |
| WO | 02/24089 A1 | 3/2002 | |
| WO | 2006/122279 | 11/2006 | |
| WO | 2007/002545 | 1/2007 | |
| WO | 2007/093857 | 8/2007 | |
| WO | WO-2009141624 A1 | 11/2009 | |
| WO | 2010/101897 | 9/2010 | |
| WO | 2012/053530 A | 4/2012 | |
| WO | 2014/096815 A2 | 6/2014 | |
| WO | WO-2014143472 A1 | 9/2014 | |
| WO | WO-2014143476 A1 | 9/2014 | |
| WO | WO-2014143477 A1 | 9/2014 | |
| WO | WO-2014149250 A1 | 9/2014 | |
| WO | WO-2014150682 A1 | 9/2014 | |
| WO | WO-2014150754 A1 | 9/2014 | |
| WO | WO-2014150774 A1 | 9/2014 | |
| WO | WO-2014151560 A1 | 9/2014 | |
| WO | WO-2014152108 A1 | 9/2014 | |
| WO | WO-2014152258 A1 | 9/2014 | |
| WO | WO-2014152433 A1 | 9/2014 | |
| WO | WO-2015047611 A1 | 4/2015 | |
| WO | WO-2017123189 A1 | 7/2017 | |

OTHER PUBLICATIONS

Potentially related U.S. Appl. No. 14/589,515, filed Jan. 5, 2015, published as 2015/0119885 dated Apr. 30, 2015.
Potentially related U.S. Appl. No. 14/829,725, filed Aug. 19, 2015, Published as 2016/0051273.
Potentially related U.S. Appl. No. 14/830,069, filed Aug. 19, 2015, Published as 2016/0051275.
Potentially related U.S. Appl. No. 14/830,255, filed Aug. 19, 2015, Published as 2016/0051314.
Potentially related U.S. Appl. No. 14/177,780, filed Feb. 11, 2014, Published as 2014/0276794 dated Sep. 18, 2014.
Potentially related U.S. Appl. No. 14/178,569, filed Feb. 12, 2014, published as 2014/0276804 dated Sep. 18, 2014.
Potentially related U.S. Appl. No. 14/178,577, filed Feb. 12, 2014, published as 2014/0276786 dated Sep. 18, 2014.
Potentially related U.S. Appl. No. 14/205,598, filed Mar. 12, 2014, published as 2014/0276795 dated Sep. 18, 2014.
Potentially related U.S. Appl. No. 14/209,071, filed Mar. 13, 2014 published as 2014/0276798 dated Sep. 18, 2014.
Potentially related U.S. Appl. No. 14/210,535, filed Mar. 14, 2014, published as 2014/0276799 dated Sep. 18, 2014.
Potentially related U.S. Appl. No. 14/210,741, filed Mar. 14, 2014, published as 2014/0276800 dated Sep. 18, 2104.
Potentially related U.S. Appl. No. 14/211,042, filed Mar. 14, 2014, published as 2014/0276772 dated Sep. 18, 2014.
Japanese Notice of Allowance dated Dec. 15, 2017 (Applicaon No. 2016-500240, filed Feb. 12, 2014).
Extended European Search Report dated Feb. 27, 2018, Application No. EP17199065.8.
Potentially related U.S. Appl. No. 14/177,780, filed Feb. 11, 2014.
Potentially related U.S. Appl. No. 14/209,071, filed Mar. 13, 2014.
Potentially related U.S. Appl. No. 14/205,598, filed Mar. 12, 2014.
Potentially related U.S. Appl. No. 14/205,919, filed Mar. 12, 2014.
Potentially related to U.S. Appl. No. 14/206,010, filed Mar. 12, 2014.
Potentially related U.S. Appl. No. 14/210,535, filed Mar. 14, 2014.
Potentially related U.S. Appl. No. 14/210,741, filed Mar. 14, 2014.
Potentially related U.S. Appl. No. 14/211,042 filed Mar. 14, 2014.
Potentially related U.S. Appl. No. 14/178,569, filed Feb. 12, 2014.
Potentially related U.S. Appl. No. 14/178,577, filed Feb. 12, 2014.
315MHZ sliding remote cover, available at website : http://www.aliexpress.com/item/Sliding-Cover-Gate-Remote-Control-Duplicator-Adjustable-Frequency-Remote-Copy-100pCS-Iot-Free-Shipping-by-DHL/566451354.html?tracelog=back_to_detail_a (accessed on Feb. 21, 2013).
Sliding Gate Remote Control Duplicator, available at website: http://www.aliexpress.com/item/315MHZ-sliding-cover-remote-controller-duplicating-remote-controller-sliding-gate-remote-garager-door-remote/491795542.html (accessed on Feb. 21, 2013).
International Searching Authority and Written Opinion, PCT/US2014/01512, dated Apr. 9, 2014.
European Office Action dated Dec. 9, 2016; Application No. 14709449.4.
"U.S. Appl. No. 14/589,482, Final Office Action dated Jul. 2, 2021", 8 pgs.
"U.S. Appl. No. 14/589,482, Non Final Office Action dated Mar. 12, 2021", 15 pgs.
"U.S. Appl. No. 14/589,482, Response filed Jun. 14, 2021 to Non Final Office Action dated Mar. 12, 2021", 15 pgs.
"U.S. Appl. No. 14/589,482, Response filed Sep. 2, 2021 to Final Office Action dated Jul. 2, 2021", 13 pgs.
U.S. Appl. No. 14/209,071 U.S. Pat. No. 9,901,388, filed Mar. 13, 2014, Hand Switched Combined Eletrosurgical Monopolar and Bipolar Device.
U.S. Appl. No. 15/658,641, filed Jul. 25, 2017, Hand Switched Combined Electrosurgical Monopolar and Biopolar Device.
U.S. Appl. No. 14/178,411 U.S. Pat. No. 10,292,757, filed Feb. 12, 2014, Electrosurgical Instrument.
U.S. Appl. No. 14/178,577 U.S. Pat. No. 10,085,793, filed Feb. 12, 2014, Offset Forceps.
U.S. Appl. No. 16/048,553, filed Jul. 30, 2018, Offset Forceps.
U.S. Appl. No. 14/206,010, filed Mar. 12, 2014, Combination Electrosurgical Device.
U.S. Appl. No. 14/205,598, U.S. Pat. No. 9,452,011, filed Mar. 12, 2014, Combination Elecrosurgical Device.
U.S. Appl. No. 14/589,515, filed Jan. 5, 2015, Combination Electrosurgical Device.
U.S. Appl. No. 14/589,482, filed Jan. 5, 2015, Combination Electrosurgical Device.
U.S. Appl. No. 14/205,919, filed Mar. 12, 2014, Combination Electrosurgical Device.
U.S. Appl. No. 14/210,535 U.S. Pat. No. 9,452,009, filed Mar. 14, 2014, Combination Electrosurgical Device.
U.S. Appl. No. 15/235,506 U.S. Pat. No. 10,271,895, filed Aug. 12, 2016, Combination Electrosurgical Device.
U.S. Appl. No. 16/395,142, filed Apr. 25, 2019, Combination Electrosurgical Device.
U.S. Appl. No. 14/210,741 U.S. Pat. No. 9,445,863, filed Mar. 14, 2014, Combination Electrosurgical Device.
U.S. Appl. No. 14/211,042 U.S. Pat. No. 9,668,805, filed Mar. 14, 2014, Combination Electrosurgical Device.
U.S. Appl. No. 14/178,569 U.S. Pat. No. 9,901,389 filed Feb. 12, 2014, Offset Forceps.
U.S. Appl. No. 14/177,780 U.S. Pat. No. 9,763,730, filed Feb. 11, 2014, Electrosurgical Instrument.

(56) References Cited

OTHER PUBLICATIONS

"U.S. Appl. No. 14/177,780, Examiner Interview Summary dated Aug. 10, 2016", 3 pgs.
"U.S. Appl. No. 14/177,780, Final Office Action dated Mar. 29, 2016", 10 pgs.
"U.S. Appl. No. 14/177,780, Non Final Office Action dated Jan. 20, 2017", 10 pgs.
"U.S. Appl. No. 14/177,780, Non Final Office Action dated Nov. 13, 2015", 11 pgs.
"U.S. Appl. No. 14/177,780, Notice of Allowance dated May 23, 2017", 7 pgs.
"U.S. Appl. No. 14/177,780, Response filed Feb. 15, 2016 to Non Final Office Action dated Nov. 13, 2015", 11 pgs.
"U.S. Appl. No. 14/177,780, Response filed Apr. 20, 2017 to Non Final Office Action dated Jan. 20, 2017", 10 pgs.
"U.S. Appl. No. 14/177,780, Response filed Aug. 29, 2016 to Final Office Action dated Mar. 29, 2016", 9 pgs.
"U.S. Appl. No. 14/178,411, Advisory Action dated Jul. 6, 2018", 3 pgs.
"U.S. Appl. No. 14/178,411, Advisory Action dated Jul. 19, 2017", 3 pgs.
"U.S. Appl. No. 14/178,411, Examiner Interview Summary dated May 24, 2018", 3 pgs.
"U.S. Appl. No. 14/178,411, Examiner Interview Summary dated Jun. 2, 2017", 4 pgs.
"U.S. Appl. No. 14/178,411, Examiner Interview Summary dated Aug. 10, 2016", 3 pgs.
"U.S. Appl. No. 14/178,411, Final Office Action dated Mar. 15, 2016", 10 pgs.
"U.S. Appl. No. 14/178,411, Final Office Action dated Apr. 12, 2017", 10 pgs.
"U.S. Appl. No. 14/178,411, Final Office Action dated Apr. 23, 2018", 11 pgs.
"U.S. Appl. No. 14/178,411, Non Final Office Action dated Nov. 16, 2015", 10 pgs.
"U.S. Appl. No. 14/178,411, Non Final Office Action dated Dec. 20, 2017", 12 pgs.
"U.S. Appl. No. 14/178,411, Non Final Office Action dated Dec. 27, 2016", 10 Pgs.
"U.S. Appl. No. 14/178,411, Notice of Allowance dated Jan. 17, 2019", 9 pgs.
"U.S. Appl. No. 14/178,411, Response filed Feb. 16, 2016 to Non Final Office Action dated Nov. 16, 2015", 10 pgs.
"U.S. Appl. No. 14/178,411, Response filed Mar. 20, 2018 to Non Final Office Action dated Dec. 20, 2017", 9 pgs.
"U.S. Appl. No. 14/178,411, Response filed Mar. 27, 2017 to Non Final Office Action dated Dec. 27, 2016", 7 pgs.
"U.S. Appl. No. 14/178,411, Response filed Jun. 25, 2018 to Final Office Action dated Apr. 23, 2018", 10 pgs.
"U.S. Appl. No. 14/178,411, Response filed Jul. 12, 2017 to Final Office Action dated Apr. 12, 2017", 8 pgs.
"U.S. Appl. No. 14/178,411, Response filed Aug. 11, 2017 to Advisory Action dated Jul. 19, 2017", 8 pgs.
"U.S. Appl. No. 14/178,411, Response filed Aug. 15, 2016 to Final Office Action dated Mar. 15, 2016", 8 pgs.
"U.S. Appl. No. 14/178,411, Supplemental Amendment filed Mar. 3, 2016", 10 pgs.
"U.S. Appl. No. 14/178,569, 312 Amendment filed Dec. 27, 2017", 8 pgs.
"U.S. Appl. No. 14/178,569, Advisory Action dated Nov. 16, 2016", 3 pgs.
"U.S. Appl. No. 14/178,569, Examiner Interview Summary dated Jul. 14, 2017", 4 pgs.
"U.S. Appl. No. 14/178,569, Examiner Interview Summary dated Aug. 8, 2016", 4 pgs.
"U.S. Appl. No. 14/178,569, Final Office Action dated Sep. 8, 2016", 16 pgs.
"U.S. Appl. No. 14/178,569, Non Final Office Action dated Apr. 7, 2017", 16 pgs.
"U.S. Appl. No. 14/178,569, Non Final Office Action dated Apr. 20, 2016", 19 pgs.
"U.S. Appl. No. 14/178,569, Notice of Allowance dated Sep. 29, 2017", 10 pgs.
"U.S. Appl. No. 14/178,569, PTO Response to Rule 312 Communication dated Jan. 24, 2018", 2 pgs.
"U.S. Appl. No. 14/178,569, Response filed Jul. 7, 2017 to Non Final Office Action dated Apr. 7, 2017", 20 pgs.
"U.S. Appl. No. 14/178,569, Response filed Jul. 20, 2016 to Non Final Office Action dated Apr. 20, 2016", 19 pgs.
"U.S. Appl. No. 14/178,569, Response filed Nov. 8, 2016 to Final Office Action dated Sep. 8, 2016". 17 pgs.
"U.S. Appl. No. 14/178,577, 312 Amendment filed Jul. 30, 2018", 9 pgs.
"U.S. Appl. No. 14/178,577, Advisory Action dated Nov. 16, 2016", 3 pgs.
"U.S. Appl. No. 14/178,577, Examiner Interview Summary dated Jul. 14, 2017", 3 pgs.
"U.S. Appl. No. 14/178,577, Examiner Interview Summary dated Aug. 4, 2016", 4 pgs.
"U.S. Appl. No. 14/178,577, Examiner Interview Summary dated Dec. 13, 2017", 3 pgs.
"U.S. Appl. No. 14/178,577, Final Office Action dated Sep. 8, 2016", 21 pgs.
"U.S. Appl. No. 14/178,577, Final Office Action dated Sep. 27, 2017", 10 pgs.
"U.S. Appl. No. 14/178,577, Non Final Office Action dated Apr. 6, 2017", 18 pgs.
"U.S. Appl. No. 14/178,577, Non Final Office Action dated Apr. 21, 2016", 19 pgs.
"U.S. Appl. No. 14/178,577, Notice of Allowance dated May 2, 2018", 16 pgs.
"U.S. Appl. No. 14/178,577, PTO Response to Rule 312 Communication dated Jul. 9, 2018", 2 pgs.
"U.S. Appl. No. 14/178,577, PTO Response to Rule 312 Communication dated Aug. 29, 2018", 2 pgs.
"U.S. Appl. No. 14/178,577, Response filed Jul. 6, 2017 to Non Final Office Action dated Apr. 6, 2017", 19 pgs.
"U.S. Appl. No. 14/178,577, Response filed Jul. 21, 2016 to Non Final Office Action dated Apr. 21, 2016", 21 pgs.
"U.S. Appl. No. 14/178,577, Response filed Nov. 7, 2016 to Final Office Action dated Sep. 8, 2016", 19 pgs.
"U.S. Appl. No. 14/178,577, Response filed Dec. 27, 2017 to Final Office Action dated Sep. 27, 2017", 15 pgs.
"U.S. Appl. No. 14/205,598, Examiner Interview Summary dated Mar. 10, 2016", 3 pgs.
"U.S. Appl. No. 14/205,598, Final Office Action dated Apr. 22, 2016", 16 pgs.
"U.S. Appl. No. 14/205,598, Non Final Office Action dated Dec. 8, 2015", 18 pgs.
"U.S. Appl. No. 14/205,598, Notice of Allowance dated Aug. 8, 2016", 10 pgs.
"U.S. Appl. No. 14/205,598, Preliminary Amendment filed Mar. 18, 2015", 6 pgs.
"U.S. Appl. No. 14/205,598, Response filed Mar. 8, 2016 to Non Final Office Action dated Dec. 8, 2015", 14 pgs.
"U.S. Appl. No. 14/205,598, Response filed Jun. 21, 2016 to Final Office Action dated Apr. 22, 2016", 12 pgs.
"U.S. Appl. No. 14/205,919, Examiner Interview Summary dated May 3, 2016", 3 pgs.
"U.S. Appl. No. 14/205,919, Final Office Action dated May 3, 2017", 16 pgs.
"U.S. Appl. No. 14/205,919, Non Final Office Action dated Jan. 29, 2016", 14 pgs.
"U.S. Appl. No. 14/205,919, Non Final Office Action dated Oct. 17, 2016", 15 pgs.
"U.S. Appl. No. 14/205,919, Response filed Jan. 17, 2017 to Non Final Office Action dated Oct. 17, 2016", 9 pgs.
"U.S. Appl. No. 14/205,919, Response filed Apr. 28, 2016 to Non Final Office Action dated Jan. 29, 2016", 11 pgs.
"U.S. Appl. No. 14/206,010, Advisory Action dated Nov. 22, 2016", 6 pgs.

(56) References Cited

OTHER PUBLICATIONS

"U.S. Appl. No. 14/206,010, Examiner Interview Summary dated May 2, 2016", 3 pgs.
"U.S. Appl. No. 14/206,010, Examiner Interview Summary dated Jul. 10, 2018", 3 pgs.
"U.S. Appl. No. 14/206,010, Examiner Interview Summary dated Jul. 24, 2018", 3 pgs.
"U.S. Appl. No. 14/206,010, Examiner Interview Summary dated Sep. 15, 2017", 3 pgs.
"U.S. Appl. No. 14/206,010, Final Office Action dated Feb. 13, 2018", 17 pgs.
"U.S. Appl. No. 14/206,010, Final Office Action dated Jul. 26, 2019", 14 pgs.
"U.S. Appl. No. 14/206,010, Final Office Action dated Aug. 26, 2016", 13 pgs.
"U.S. Appl. No. 14/206,010, Non Final Office Action dated Jan. 2, 2019", 15 pgs.
"U.S. Appl. No. 14/206,010, Non Final Office Action dated Jan. 29, 2016", 11 pgs.
"U.S. Appl. No. 14/206,010, Non Final Office Action dated Jun. 2, 2017", 13 pgs.
"U.S. Appl. No. 14/206,010, Response filed Apr. 18, 2019 to Non Final Office Action dated Jan. 2, 2019", 10 pgs.
"U.S. Appl. No. 14/206,010, Response filed Apr. 28, 2016 to Non Final Office Action dated Jan. 29, 2016", 9 pgs.
"U.S. Appl. No. 14/206,010, Response filed Jun. 26, 2018 to Final Office Action dated Feb. 13, 2018", 9 pgs.
"U.S. Appl. No. 14/206,010, Response filed Sep. 8, 2017 to Non Final Office Action dated Jun. 2, 2017", 11 pgs.
"U.S. Appl. No. 14/206,010, Response filed Oct. 13, 2016 to Final Office Action dated Aug. 26, 2016", 6 pgs.
"U.S. Appl. No. 14/206,010, Response filed Dec. 19, 2016 to Advisory Action dated Nov. 22, 2016", 8 pgs.
"U.S. Appl. No. 14/209,071, Corrected Notice of Allowability dated Jun. 2, 2017", 2 pgs.
"U.S. Appl. No. 14/209,071, Examiner Interview Summary dated Sep. 20, 2016", 3 pgs.
"U.S. Appl. No. 14/209,071, Final Office Action dated Dec. 30, 2016", 10 pgs.
"U.S. Appl. No. 14/209,071, Non Final Office Action dated Mar. 25, 2016", 15 pgs.
"U.S. Appl. No. 14/209,071, Notice of Allowance dated Apr. 18, 2017", 7 pgs.
"U.S. Appl. No. 14/209,071, Notice of Allowance dated Nov. 8, 2017", 5 pgs.
"U.S. Appl. No. 14/209,071, Response filed Feb. 28, 2017 to Final Office Action dated Dec. 30, 2016", 6 pgs.
"U.S. Appl. No. 14/209,071, Response filed Sep. 26, 2016 to Non Final Office Action dated Mar. 25, 2016", 7 pgs.
"U.S. Appl. No. 14/210,535, 312 Amendment filed Jul. 5, 2016", 7 pgs.
"U.S. Appl. No. 14/210,535, Examiner Interview Summary dated May 10, 2016", 3 pgs.
"U.S. Appl. No. 14/210,535, Non Final Office Action dated Feb. 4, 2016", 12 pgs.
"U.S. Appl. No. 14/210,535, Notice of Allowance dated May 25, 2016", 11 pgs.
"U.S. Appl. No. 14/210,535, PTO Response to Rule 312 Communication dated Jul. 19, 2016", 2 pgs.
"U.S. Appl. No. 14/210,535, Response filed May 4, 2016 to Non Final Office Action dated Feb. 4, 2016", 14 pgs.
"U.S. Appl. No. 14/210,741, Examiner Interview Summary dated May 10, 2016", 3 pgs.
"U.S. Appl. No. 14/210,741, Non Final Office Action dated Feb. 11, 2016", 11 pgs.
"U.S. Appl. No. 14/210,741, Notice of Allowance dated May 24, 2016", 10 pgs.
"U.S. Appl. No. 14/210,741, Response filed May 4, 2016 to Non Final Office Action dated Feb. 11, 2016", 12 pgs.
"U.S. Appl. No. 14/211,042, Examiner Interview Summary dated Dec. 23, 2016", 3 pgs.
"U.S. Appl. No. 14/211,042, Non Final Office Action dated Jul. 21, 2016", 12 pgs.
"U.S. Appl. No. 14/211,042, Notice of Allowance dated Mar. 27, 2017", 13 pgs.
"U.S. Appl. No. 14/211,042, Response filed Dec. 20, 2016 to Non Final Office Action dated Jul. 21, 2016", 9 pgs.
"U.S. Appl. No. 14/589,482, Advisory Action dated Jan. 24, 2018", 3 pgs.
"U.S. Appl. No. 14/589,482, Examiner Interview Summary dated Jul. 25, 2017", 3 pgs.
"U.S. Appl. No. 14/589,482, Examiner Interview Summary dated Dec. 28, 2017", 3 pgs.
"U.S. Appl. No. 14/589,482, Final Office Action dated Oct. 21, 2019", 14 pgs.
"U.S. Appl. No. 14/589,482, Final Office Action dated Nov. 2, 2017", 13 pgs.
"U.S. Appl. No. 14/589,482, Non Final Office Action dated Feb. 26, 2019", 13 pgs.
"U.S. Appl. No. 14/589,482, Non Final Office Action dated Mar. 13, 2020", 15 pgs.
"U.S. Appl. No. 14/589,482, Non Final Office Action dated Apr. 19, 2017", 12 pgs.
"U.S. Appl. No. 14/589,482, Non Final Office Action dated Aug. 6, 2018", 15 pgs.
"U.S. Appl. No. 14/589,482, Preliminary Amendment filed Jan. 5, 2015", 8 pgs.
"U.S. Appl. No. 14/589,482, Response filed Jun. 4, 2019 to Non Final Office Action dated Feb. 26, 2019", 11 pgs.
"U.S. Appl. No. 14/589,482, Response filed Jun. 15, 2020 to Non Final Office Action dated Mar. 13, 2020", 18 pgs.
"U.S. Appl. No. 14/589,482, Response filed Jul. 20, 2017 to Non Final Office Action dated Apr. 19, 2017", 10 pgs.
"U.S. Appl. No. 14/589,482, Response filed Oct. 24, 2018 to Non Final Office Action dated Aug. 6, 2018", 12 pgs.
"U.S. Appl. No. 14/589,482, Response filed Dec. 20, 2017 to Final Office Action dated Nov. 2, 2017", 9 pgs.
"U.S. Appl. No. 14/589,482, Response filed Dec. 23, 2019 to Final Office Action dated Oct. 21, 2019", 17 pgs.
"U.S. Appl. No. 14/589,515, Advisory Action dated Feb. 5, 2018", 3 pgs.
"U.S. Appl. No. 14/589,515, Examiner Interview Summary dated Jul. 7, 2017", 3 pgs.
"U.S. Appl. No. 14/589,515, Final Office Action dated Mar. 21, 2019", 14 pgs.
"U.S. Appl. No. 14/589,515, Final Office Action dated Oct. 5, 2017", 13 pgs.
"U.S. Appl. No. 14/589,515, Non Final Office Action dated Mar. 24, 2017", 17 pgs.
"U.S. Appl. No. 14/589,515, Non Final Office Action dated Sep. 4, 2018", 15 pgs.
"U.S. Appl. No. 14/589,515, Notice of Allowance dated Mar. 31, 2020", 5 pgs.
"U.S. Appl. No. 14/589,515, Notice of Allowance dated Nov. 25, 2019", 8 pgs.
"U.S. Appl. No. 14/589,515, Preliminary Amendment filed Jan. 5, 2015", 7 pgs.
"U.S. Appl. No. 14/589,515, Response filed May 20, 2019 to Final Office Action dated Mar. 21, 2019", 11 pgs.
"U.S. Appl. No. 14/589,515, Response filed Jun. 20, 2017 to Non Final Office Action dated Mar. 24, 2017", 12 pgs.
"U.S. Appl. No. 14/589,515, Response filed Nov. 30, 2018 to Non Final Office Action dated Sep. 4, 2018", 12 pgs.
"U.S. Appl. No. 14/589,515, Response filed Dec. 4, 2017 to Final Office Action dated Oct. 5, 2017", 12 pgs.
"U.S. Appl. No. 14/589,515, Supplemental Amendment filed Jun. 29, 2017", 12 pgs.
"U.S. Appl. No. 15/235,506, Corrected Notice of Allowability dated Dec. 28, 2018", 4 pgs.
"U.S. Appl. No. 15/235,506, Examiner Interview Summary dated Nov. 26, 2018", 3 pgs.

(56) References Cited

OTHER PUBLICATIONS

"U.S. Appl. No. 15/235,506, Non Final Office Action dated Aug. 10, 2018", 10 pgs.
"U.S. Appl. No. 15/235,506, Notice of Allowance dated Dec. 19, 2018", 11 pgs.
"U.S. Appl. No. 15/235,506, Preliminary Amendment filed Aug. 12, 2016", 7 pgs.
"U.S. Appl. No. 15/235,506, Response filed Nov. 27, 2018 to Non Final Office Action dated Aug. 10, 2018", 9 pgs.
"U.S. Appl. No. 15/658,641, Corrected Notice of Allowability dated May 8, 2020", 3 pgs.
"U.S. Appl. No. 15/658,641, Non Final Office Action dated Sep. 17, 2019", 8 pgs.
"U.S. Appl. No. 15/658,641, Notice of Allowance dated Feb. 26, 2020", 9 pgs.
"U.S. Appl. No. 15/658,641, Notice of Allowance dated Jul. 1, 2020", 6 pgs.
"U.S. Appl. No. 15/658,641, Preliminary Amendment filed Jul. 25, 2017", 5 pgs.
"U.S. Appl. No. 15/658,641, Response filed Dec. 17, 2019 to Non Final Office Action dated Sep. 17, 2019", 9 pgs.
"U.S. Appl. No. 16/048,553, Preliminary Amendment filed Jul. 30, 2018", 6 pgs.
"U.S. Appl. No. 16/395,142, Preliminary Amendment filed May 30, 2019", 8 pgs.
"Australian Application Serial No. 2014235755, First Examination Report dated Nov. 27, 2017", 3 pgs.
"Australian Application Serial No. 2014235755, Office Action dated Jun. 29, 2018", 3 pgs.
"Australian Application Serial No. 2014235755, Response filed May 29, 2018 to First Examination Report dated Nov. 27, 2017", 16 pgs.
"Australian Application Serial No. 2014235755, Response filed Oct. 8, 2018 to Office Action dated Jun. 29, 2018", 14 pgs.
"Australian Application Serial No. 2015205939, Examination Report dated Dec. 8, 2016", 3 pgs.
"Australian Application Serial No. 2015205939, Response filed Feb. 17, 2017 to First Examination Report dated Dec. 8, 2016", 13 pgs.
"Australian Application Serial No. 2015207838, First Examination Report dated Dec. 8, 2016" 3 pgs.
"Australian Application Serial No. 2015207838, Response filed Feb. 17, 2017 to First Examination Report dated Dec. 8, 2016", 11 pgs.
"Chinese Application Serial No. 201480007117.0, Amendment filed Aug. 11, 2017", with machine translation, 17 pgs.
"Chinese Application Serial No. 201480007117.0, Office Action dated Mar. 13, 2017", with English translation of claims, 9 pgs.
"Chinese Application Serial No. 201480007117.0, Response filed Jul. 26, 2017 to Office Action dated Mar. 13, 2017", with machine translation, 93 pgs.
"Chinese Application Serial No. 201480008984.6, Office Action dated Jun. 8, 2017", with English translation of claims, 7 pgs.
"Chinese Application Serial No. 201480008984.6, Office Action dated Oct. 17, 2016", with English translation of claims, 10 pgs.
"Chinese Application Serial No. 201480008984.6, Response filed Jun. 27, 2017 to Office Action dated Jun. 8, 2017", with machine translation, 17 pgs.
"Chinese Application Serial No. 201480011492.2, Office Action dated Jun. 1, 2017", with English translation of claims, 15 pgs.
"Chinese Application Serial No. 201480011492.2, Office Action dated Oct. 26, 2016", with English translation of claims, 14 pgs.
"Chinese Application Serial No. 201480011492.2, Response filed Mar. 9, 2017 to Office Action dated Oct. 26, 2016", with English translation of claims, 4 pgs.
"Chinese Application Serial No. 201480011492.2, Response filed Aug. 8, 2017 to Office Action dated Jun. 1, 2017", with English translation of claims, 13 pgs.
"Chinese Application Serial No. 201480015016.8, Office Action dated Jan. 25, 2017", with English translation of claims, 10 pgs.
"Chinese Application Serial No. 201480015016.8, Office Action dated Mar. 26, 2018", with English translation of claims, 8 pgs.
"Chinese Application Serial No. 201480015016.8, Office Action dated Oct. 13, 2017", with English translation of claims, 14 pgs.
"Chinese Application Serial No. 201480015016.8, Response filed Dec. 22, 2017", WIPO transalation, 14 pgs.
"Chinese Application Serial No. 201480015301.X, Office Action dated Dec. 2, 2016", w/ English translation, 18 pgs.
"Chinese Application Serial No. 201480015301.X, Office Action dated Jan. 29, 2018", with English translation of claims, 9 pgs.
"Chinese Application Serial No. 201480015301.X, Office Action dated Apr. 10, 2017", with English translation of claims, 14 pgs.
"Chinese Application Serial No. 201480015301.X, Office Action dated Aug. 10, 2017", with English translation of claims, 11 pgs.
"Chinese Application Serial No. 201480015301.X, Office Action dated Dec. 2, 2016", with English translation of claims, 15 pgs.
"Chinese Application Serial No. 201480015301.X, Reexamination Request filed Oct. 10, 2017", with English translation of claims, 12 pgs.
"Chinese Application Serial No. 201480015301.X, Response filed Mar. 21, 2017 to Office Action dated Dec. 2, 2016", with machine translation, 18 pgs.
"Chinese Application Serial No. 201480015301.X, Response filed Mar. 22, 2018 to Office Action dated Jan. 29, 2018", w/ English translation, 13 pgs.
"Chinese Application Serial No. 201480015301.X, Response filed Jun. 23, 2017 to Office Action dated Apr. 10, 2017", with machine translation, 10 pgs.
"Chinese Application Serial No. 201480021729.5, Office Action dated Jul. 12, 2017", w/ English translation, 17 pgs.
"Chinese Application Serial No. 201480021729.5, Office Action dated Dec. 15, 2017", w/ English translation, 8 pgs.
"Chinese Application Serial No. 201480021729.5, Office Action dated Dec. 26, 2016", w/ English translation, 14 pgs.
"Chinese Application Serial No. 201480021729.5, Response filed Feb. 22, 2018 to Office Action dated Dec. 15, 2017", W/English Translation, 23 pgs.
"Chinese Application Serial No. 201480021729.5, Response filed Mar. 23, 2017 to Office Action dated Dec. 26, 2016", W/English Translation, 8 pgs.
"Chinese Application Serial No. 201480021729.5, Response filed Sep. 4, 2017 to Office Action dated Jul. 12, 2017", W/English Translation, 9 pgs.
"Chinese Application Serial No. 201480023592.7, Office Action dated May 14, 2018", W/ English Translation, 11 pgs.
"Chinese Application Serial No. 201480023592.7, Office Action dated Sep. 11, 2017", W/ English Translation, 9 pgs.
"Chinese Application Serial No. 201480027040.3, Office Action dated Mar. 2, 2017", w/ English translation, 19 pgs.
"Chinese Application Serial No. 201480027040.3, Response filed Jul. 14, 2017 to Office Action dated Mar. 2, 2017", w/ English translation, 13 pgs.
"Chinese Application Serial No. 201480027558.7, Office Action dated Feb. 24, 2018", w/ English Translation, 8 pgs.
"Chinese Application Serial No. 201480027558.7, Office Action dated Aug. 1, 2017", w/ English Translation, 11 pgs.
"Chinese Application Serial No. 201480027558.7, Office Action dated Dec. 28, 2016", w/ English Translation, 11 pgs.
"Chinese Application Serial No. 201480027558.7, Response filed May 11, 2017 to Office Action dated Dec. 28, 2016", with machine translation, 15 pgs.
"Chinese Application Serial No. 201480027558.7, Response filed May 11, 2018 to Office Action dated Feb. 24, 2018", with machine translation, 19 pgs.
"Chinese Application Serial No. 201480027558.7, Response filed Oct. 12, 2017 Office Action dated Aug. 1, 2017", with machine translation, 15 pgs.
"Chinese Application Serial No. 201480028116.4, Office Action dated Feb. 14, 2017", with English translation of claims, 11 pgs.
"Chinese Application Serial No. 201480028116.4, Response filed Jun. 27, 2017 to Office Action dated Feb. 14, 2017", with machine translation, 25 pgs.

(56) References Cited

OTHER PUBLICATIONS

"Chinese Application Serial No. 201510671557.2, Office Action dated Apr. 6, 2017", with English translation of claims, 8 pgs.
"Chinese Application Serial No. 201510671557.2, Response filed Aug. 1, 2017 to Office Action dated Apr. 6, 2017", with machine translation, 21 pgs.
"Chinese Application Serial No. 201510673032.2, Amendment filed Aug. 16, 2017", with machine translation, 19 pgs.
"Chinese Application Serial No. 201510673032.2, Office Action dated Apr. 5, 2017", with English translation of claims, 7 pgs.
"Chinese Application Serial No. 201510673032.2, Response filed Jul. 26, 2017 to Office Action dated Apr. 5, 2017", with machine translation, 17 pgs.
"Chinese Application Serial No. 201810113314.0, Office Action dated Apr. 10, 2020", W/English Translation, 10 pgs.
"European Application Serial No. 14706460.4, Communication Pursuant to Article 94(3) EPC dated Apr. 19, 2016", 6 pgs.
"European Application Serial No. 14706460.4, Intention to Grant dated Dec. 9, 2016", 45 pgs.
"European Application Serial No. 14706460.4, Response filed Aug. 13, 2016 to Communication Pursuant to Article 94(3) EPC dated Apr. 19, 2016", 57 pgs.
"European Application Serial No. 14706759.9, Communication Pursuant to Article 94(3) EPC dated Apr. 19, 2016", 7 pgs.
"European Application Serial No. 14706759.9, Intention to Grant dated Feb. 2, 2017", 43 pgs.
"European Application Serial No. 14706759.9, Intention to Grant dated May 31, 2017", 40 pgs.
"European Application Serial No. 14706759.9, Response filed May 3, 2017 to Intention to Grant dated Feb. 2, 2017", 9 pgs.
"European Application Serial No. 14706759.9, Response filed Aug. 18, 2016 to Communication Pursuant to Article 94(3) EPC dated Apr. 19, 2016", 46 pgs.
"European Application Serial No. 14708170.7, Communication Pursuant to Article 94(3) EPC dated Apr. 19, 2016", 6 pgs.
"European Application Serial No. 14708170.7, Office Action dated Dec. 20, 2016", 4 pgs.
"European Application Serial No. 14708170.7, Response filed Mar. 15, 2017 to Office Action dated Dec. 20, 2016", 5 pgs.
"European Application Serial No. 14708170.7, Response filed Aug. 13, 2016 to Communication Pursuant to Article 94(3) EPC dated Apr. 19, 2016", 57 pgs.
"European Application Serial No. 14709449.4, Communication Pursuant to Article 94(3) EPC dated Apr. 19, 2016", 6 pgs.
"European Application Serial No. 14709449.4, Intention to Grant dated Jul. 26, 2017", 44 pgs.
"European Application Serial No. 14709449.4, Response filed Mar. 28, 2017 to Communication Pursuant to Article 94(3) EPC dated Dec. 9, 2016", 4 pgs.
"European Application Serial No. 14709449.4, Response filed Aug. 18, 2016 to Communication Pursuant to Article 94(3) EPC dated Apr. 19, 2016", 25 pgs.
"European Application Serial No. 14716688.8, Communication Pursuant to Article 94(3) EPC dated Apr. 19, 2016", 6 pgs.
"European Application Serial No. 14716688.8, Communication Pursuant to Article 94(3) EPC dated Nov. 25, 2016", 4 pgs.
"European Application Serial No. 14716688.8, Intention to Grant dated Jul. 31, 2017", 86 pgs.
"European Application Serial No. 14716688.8, Response filed Mar. 16, 2017 to Communication Pursuant to Article 94(3) EPC dated Nov. 25, 2016", 14 pgs.
"European Application Serial No. 14716688.8, Response filed Aug. 15, 2016 to Communication Pursuant to Article 94(3) EPC dated Apr. 19, 2016", 9 pgs.
"European Application Serial No. 14719559.8, Communication Pursuant to Article 94(3) EPC dated Jul. 11, 2017", 5 pgs.
"European Application Serial No. 14719559.8, Communication Pursuant to Article 94(3) EPC dated Nov. 18, 2016", 5.
"European Application Serial No. 14719559.8, Intention to Grant dated Mar. 21, 2018", 83 pgs.
"European Application Serial No. 14719559.8, Response filed Mar. 6, 2017 to Communication Pursuant to Article 94(3) EPC dated Nov. 18, 2016", 8 pgs.
"European Application Serial No. 14719559.8, Response filed Nov. 7, 2017 to Communication Pursuant to Article 94(3) EPC dated Jul. 11, 2017", 98 pgs.
"European Application Serial No. 14719559.8, Response to Communication pursuant to Rules 161(1) and 162 EPC filed Apr. 10, 2016", 50 pgs.
"European Application Serial No. 14720793.0, Communication Pursuant to Article 94(3) EPC dated Apr. 19, 2016", 6 pgs.
"European Application Serial No. 14720793.0, Communication Pursuant to Article 94(3) EPC dated Dec. 13, 2016", 5 pgs.
"European Application Serial No. 14720793.0, Intention to Grant dated Feb. 28, 2018", 23 pgs.
"European Application Serial No. 14720793.0, Intention to Grant dated Sep. 22, 2017", 25 pgs.
"European Application Serial No. 14720793.0, Response filed Jan. 9, 2018 to Intention to Grant dated Sep. 22, 2017", 14 pgs.
"European Application Serial No. 14720793.0, Response filed Mar. 22, 2017 to Communication Pursuant to Article 94(3) EPC dated Dec. 13, 2016", 30 pgs.
"European Application Serial No. 14720793.0, Response filed Aug. 18, 2016 to Communication Pursuant to Article 94(3) EPC dated Apr. 19, 2016", 29 pgs.
"European Application Serial No. 14720816.9, Communication Pursuant to Article 94(3) EPC dated Jan. 27, 2016", 5 pgs.
"European Application Serial No. 14720816.9, Intention to Grant dated Aug. 22, 2016", 56 pgs.
"European Application Serial No. 14720816.9, Response filed May 20, 2016 to Communication Pursuant to Article 94(3) EPC dated Jan. 27, 2016", 39 pgs.
"European Application Serial No. 14720821.9, Communication Pursuant to Article 94(3) EPC dated Apr. 15, 2016", 5 pgs.
"European Application Serial No. 14720821.9, Communication Pursuant to Article 94(3) EPC dated Nov. 16, 2016", 5 pgs.
"European Application Serial No. 14720821.9, Intention to Grant dated Sep. 26, 2017", 54 pgs.
"European Application Serial No. 14720821.9, Response filed Feb. 28, 2017 to Communication Pursuant to Article 94(3) EPC dated Nov. 16, 2016", 8 pgs.
"European Application Serial No. 14720821.9, Response filed Aug. 4, 2016 to Communication Pursuant to Article 94(3) EPC dated Apr. 15, 2016", 40 pgs.
"European Application Serial No. 14722009.9, Communication pursuant to Article 94(3) EPC dated May 10, 2016", 4 pgs.
"European Application Serial No. 14722009.9, Communication Pursuant to Article 94(3) EPC dated Dec. 2, 2015", 5 pgs.
"European Application Serial No. 14722009.9, Intention to Grant dated Nov. 30, 2016", 83 pgs.
"European Application Serial No. 14722009.9, Response filed Mar. 16, 2016 to Communication Pursuant to Article 94(3) EPC dated Dec. 2, 2015", 8 pgs.
"European Application Serial No. 14722009.9, Response filed Sep. 7, 2016 to Communication Pursuant to Article 94(3) EPC dated May 10, 2016", 14 pgs.
"European Application Serial No. 15178743.9, Extended European Search Report dated Nov. 27, 2015", 6 pgs.
"European Application Serial No. 15178743.9, Intention to Grant dated Mar. 3, 2017", 84 pgs.
"European Application Serial No. 15178743.9, Intention to Grant dated Jul. 25, 2017", 21 pgs.
"European Application Serial No. 15178743.9, Response filed Jun. 30, 2017 to Intention to Grant dated Mar. 3, 2017", 16 pgs.
"European Application Serial No. 15178743.9, Response filed Jul. 8, 2016 to Extended European Search Report dated Nov. 27, 2015", 104 pgs.
"European Application Serial No. 15180662.7, Extended European Search Report dated Dec. 23, 2015", 7 pgs.
"European Application Serial No. 15180662.7, Intention to Grant dated Mar. 20, 2017", 81 pgs.

(56) References Cited

OTHER PUBLICATIONS

"European Application Serial No. 15180662.7, Response filed Jul. 7, 2016 to Extended European Search Report dated Dec. 23, 2015", 100 pgs.
"European Application Serial No. 16197628.7, Communication Pursuant to Article 94(3) EPC dated Oct. 9, 2018", 5 pgs.
"European Application Serial No. 16197628.7, Extended European Search Report dated Mar. 2, 2017", 7 pgs.
"European Application Serial No. 16197628.7, Response filed Jan. 30, 2019 to Communication Pursuant to Article 94(3) EPC dated Oct. 9, 2018", 8 pgs.
"European Application Serial No. 16197628.7, Response filed Oct. 17, 2017 to Extended European Search Report dated Mar. 2, 2017", 37 pgs.
"European Application Serial No. 17161375.5, Extended European Search Report dated Jul. 10, 2017", 7 pgs.
"European Application Serial No. 17161375.5, Office Action dated Jan. 4, 2019", 6 pgs.
"European Application Serial No. 17161375.5, Response filed Jan. 31, 2018 to Extended European Search Report dated Jul. 10, 2017", 9 pgs.
"European Application Serial No. 17161375.5, Response filed Apr. 26, 2019 to Office Action dated Jan. 4, 2019", 7 pgs.
"European Application Serial No. 17199065.8, Intention to Grant dated Mar. 26, 2019", 43 pgs.
"European Application Serial No. 17199065.8, Intention to Grant dated May 27, 2019", 43 pgs.
"European Application Serial No. 17199065.8, Response filed Oct. 16, 2018 to Extended European Search Report dated Feb. 27, 2018", 25 pgs.
"European Application Serial No. 18186355.6, Extended European Search Report dated Nov. 28, 2018", 5 pgs.
"European Application Serial No. 18186355.6, Response filed Jul. 12, 2019 to Extended European Search Report dated Nov. 28, 2018", 101 pgs.
"Indian Application Serial No. 4353/CHENP/2015, First Examination Report dated Jan. 31, 2020", 5 pgs.
"Indian Application Serial No. 4900/CHENP/2015, First Examination Report dated Feb. 12, 2020", 6 pgs.
"International Application Serial No. PCT/US2014/015916, International Preliminary Report on Patentability dated Sep. 15, 2015", 8 pgs.
"International Application Serial No. PCT/US2014/015812, International Preliminary Report on Patentability dated Sep. 24, 2015", 9 pgs.
"International Application Serial No. PCT/US2014/015812, International Search Report dated Apr. 9, 2014", 5 pgs.
"International Application Serial No. PCT/US2014/015812, Written Opinion dated Apr. 9, 2014", 7 pgs.
"International Application Serial No. PCT/US2014/015916, International Search Report dated May 12, 2014", 12 pgs.
"International Application Serial No. PCT/US2014/015916, Written Opinion dated May 12, 2014", 13 pgs.
"International Application Serial No. PCT/US2014/015923, International Preliminary Report on Patentability dated Sep. 15, 2015", 7 pgs.
"International Application Serial No. PCT/US2014/015923, International Search Report dated May 2, 2014", 4 pgs.
"International Application Serial No. PCT/US2014/015923, Written Opinion dated May 2, 2014", 6 pgs.
"International Application Serial No. PCT/US2014/015948, International Preliminary Report on Patentability dated Sep. 24, 2015", 9 pgs.
"International Application Serial No. PCT/US2014/015948, International Search Report dated Apr. 30, 2014", 5 pgs.
"International Application Serial No. PCT/US2014/015948, Written Opinion dated Apr. 30, 2014", 7 pgs.
"International Application Serial No. PCT/US2014/023958, International Preliminary Report on Patentability dated Mar. 5, 2015", 14 pgs.
"International Application Serial No. PCT/US2014/023958, International Search Report dated Jul. 21, 2014", 4 pgs.
"International Application Serial No. PCT/US2014/023958, Written Opinion dated Jul. 21, 2014", 6 pgs.
"International Application Serial No. PCT/US2014/024134, International Preliminary Report on Patentability dated Sep. 24, 2015", 7 pgs.
"International Application Serial No. PCT/US2014/024134, International Search Report dated Apr. 30, 2014", 4 pgs.
"International Application Serial No. PCT/US2014/024134, International Search Report dated Jun. 11, 2014", 4 pgs.
"International Application Serial No. PCT/US2014/024134, Written Opinion dated Apr. 30, 2014", 5 pgs.
"International Application Serial No. PCT/US2014/024134, Written Opinion dated Jun. 11, 2014", 5 pgs.
"International Application Serial No. PCT/US2014/024197, International Preliminary Report on Patentability dated Sep. 24, 2015", 7 pgs.
"International Application Serial No. PCT/US2014/024197, International Search Report dated Jul. 21, 2014", 4 pgs.
"International Application Serial No. PCT/US2014/024197, Written Opinion dated Jul. 21, 2014", 5 pgs.
"International Application Serial No. PCT/US2014/025999, International Search Report dated Jul. 22, 2014", 4 pgs.
"International Application Serial No. PCT/US2014/025999, Written Opinion dated Jul. 22, 2014", 6 pgs.
"International Application Serial No. PCT/US2014/026960, International Preliminary Report on Patentability dated Sep. 24, 2015", 6 pgs.
"International Application Serial No. PCT/US2014/026960, International Search Report dated Jul. 21, 2014", 4 pgs.
"International Application Serial No. PCT/US2014/026960, Written Opinion dated Jul. 21, 2014", 5 pgs.
"International Application Serial No. PCT/US2014/027131, International Preliminary Report on Patentability dated Sep. 24, 2015", 7 pgs.
"International Application Serial No. PCT/US2014/027131, International Search Report dated Jul. 21, 2014", 4 pgs.
"International Application Serial No. PCT/US2014/027131, Written Opinion dated Jul. 21, 2014", 5 pgs.
"International Application Serial No. PCT/US2014/027336, International Preliminary Report on Patentability dated Sep. 15, 2015", 6 pgs.
"International Application Serial No. PCT/US2014/027336, International Search Report dated Jul. 30, 2014", 4 pgs.
"International Application Serial No. PCT/US2014/027336, Written Opinion dated Jul. 30, 2014", 5 pgs.
"Japanese Application Serial No. 2015-218856, Office Action dated Aug. 29, 2017", with English translation of claims, 11 pgs.
"Japanese Application Serial No. 2015-218856, Office Action dated Dec. 20, 2016", with English translation of claims, 9 pgs.
"Japanese Application Serial No. 2015-218855, Amendment filed Mar. 25, 2016", w/ English Translation, 6 pgs.
"Japanese Application Serial No. 2015-218855, Office Action dated Oct. 25, 2016", with English translation of claims, 4 pgs.
"Japanese Application Serial No. 2015-218855, Response filed Jan. 23, 2017 to Office Action dated Oct. 25, 2016", w/ English Translation, 8 pgs.
"Japanese Application Serial No. 2015-218856, Examiners Decision of Final Refusal dated Jul. 17, 2018", with English translation, 4 pgs.
"Japanese Application Serial No. 2015-218856, Office Action dated Jul. 10, 2018", with English translation of claims, 7 pgs.
"Japanese Application Serial No. 2015-218856, Office Action dated Sep. 5, 2017", with English translation of claims, 9 pgs.
"Japanese Application Serial No. 2015-218856, Office Action dated Dec. 20, 2016", W/English Translation, 6 pgs.
"Japanese Application Serial No. 2015-218856, Response filed Feb. 1, 2018 to Office Action dated Sep. 5, 2017", W/English Translation, 17 pgs.
"Japanese Application Serial No. 2015-218856, Response filed Apr. 13, 2017 to Office Action dated Dec. 20, 2016", W/English Translation, 10 pgs.

(56) References Cited

OTHER PUBLICATIONS

"Japanese Application Serial No. 2016-230392, Notification of Reasons for Refusal dated Oct. 3, 2017", with English translation of claims, 8 pgs.
"Japanese Application Serial No. 2016-230392, Office Action dated Oct. 3, 2017", with English translation of claims, 8 pgs.
"Japanese Application Serial No. 2016-230392, Response filed Mar. 2, 2018 to Notification of Reasons for Refusal dated Oct. 3, 2017", with English translation of claims, 7 pgs.
"Japanese Application Serial No. 2016-500236, Notice of Reason for Rejection dated Apr. 9, 2017", w/ English Translation, 10 pgs.
"Japanese Application Serial No. 2016-500236, Notice of Reason for Rejection dated Oct. 25, 2016", with English translation of claims, 11 pgs.
"Japanese Application Serial No. 2016-500236, Response filed Feb. 20, 2017 to Notice of Reason for Rejection dated Oct. 25, 2016", w/ English Translation, 14 pgs.
"Japanese Application Serial No. 2016-500236, Response filed Aug. 9, 2017 to Notice of Reason for Rejection dated May 9, 2017", w/ English Translation, 7 pgs.
"Japanese Application Serial No. 2016-500239, Office Action dated May 16, 2017", with English translation of claims, 4 pgs.
"Japanese Application Serial No. 2016-500239, Office Action dated Oct. 18, 2016", with English translation of claims, 8 pgs.
"Japanese Application Serial No. 2016-500239, Response filed Jan. 18, 2017 to Office Action dated Oct. 18, 2016", with English translation of claims, 7 pgs.
"Japanese Application Serial No. 2016-500239, Response filed Jun. 16, 2017 to Office Action dated May 16, 2017", with English translation of claims, 5 pgs.
"Japanese Application Serial No. 2016-500240, Notice of Reason for Rejection dated May 9, 2017", W/ English Translation, 7 pgs.
"Japanese Application Serial No. 2016-500240, Notice of Reason for Rejection dated Oct. 25, 2016", W/ English Translation, 8 pgs.
"Japanese Application Serial No. 2016-500240, Office Action dated Dec. 15, 2017", with English translation of claims, 5 pgs.
"Japanese Application Serial No. 2016-500240, Response filed Feb. 15, 2017 to Notice of Reason for Rejection dated Oct. 25, 2016", W/ English Translation, 15 pgs.
"Japanese Application Serial No. 2016-500240, Response filed Jul. 12, 2017 to Notice of Reason for Rejection dated May 9, 2017", W/ English Translation, 10 pgs.
"Japanese Application Serial No. 2016-500243, Notice of Reason for Rejection dated Oct. 25, 2016", W/ English Translation, 8 pgs.
"Japanese Application Serial No. 2016-500243, Response filed Feb. 23, 2017 to Notice of Reason for Rejection dated Oct. 25, 2016", W/ English Translation, 10 pgs.
"Japanese Application Serial No. 2016-501393, Office Action dated Apr. 25, 2017", w/ English translation, 5 pgs.
"Japanese Application Serial No. 2016-501393, Office Action dated Sep. 6, 2016", w/ English translation, 10 pgs.
"Japanese Application Serial No. 2016-501393, Response filed Nov. 30, 2016 to Office Action dated Sep. 6, 2016", w/ English translation, 8 pgs.
"Japanese Application Serial No. 2016-501425, Office Action dated Jun. 29, 2017", with English translation of claims, 8 pgs.
"Japanese Application Serial No. 2016-501425, Office Action dated Nov. 22, 2016", with English translation of claims, 10 pgs.
"Japanese Application Serial No. 2016-501425, Response filed Apr. 18, 2017 to Office Action dated Nov. 22, 2016", with English translation of claims, 14 pgs.
"Japanese Application Serial No. 2016-501425, Response filed Oct. 17, 2017 to Office Action dated Jun. 29, 2017", with English translation of claims, 7 pgs.
"Japanese Application Serial No. 2016-501435, Office Action dated Jul. 13, 2018", with English translation of claims, 6 pgs.
"Japanese Application Serial No. 2016-501435, Office Action dated Jul. 24, 2018", with English translation of claims, 6 pgs.
"Japanese Application Serial No. 2016-501435, Office Action dated Sep. 14, 2017", with English translation of claims, 8 pgs.

"Japanese Application Serial No. 2016-501435, Office Action dated Oct. 3, 2017", with English translation of claims, 8 pgs.
"Japanese Application Serial No. 2016-501435, Response filed Feb. 23, 2018 to Office Action dated Sep. 14, 2017", with English translation of claims, 10 pgs.
"Japanese Application Serial No. 2016-501435, Response filed Oct. 18, 2018 to Office Action dated Jul. 13, 2018", with English translation of claims, 5 pgs.
"Japanese Application Serial No. 2016-502020, Office Action dated Nov. 1, 2016", with English translation of claims, 10 pgs.
"Japanese Application Serial No. 2016-502020, Response filed Jan. 30, 2017 to Office Action dated Nov. 1, 2016", with English translation of claims, 10 pgs.
"Japanese Application Serial No. 2016-502290, Notification of Reasons for Rejection dated Aug. 30, 2016", with English translation of claims, 6 pgs.
"Japanese Application Serial No. 2016-502290, Response filed Nov. 28, 2016 to Notification of Reasons for Rejection dated Aug. 24, 2016", with English translation of claims, 9 pgs.
"Japanese Application Serial No. 2016-502344, Amendment filed Nov. 13, 2015", with English translation of claims, 8 pgs.
"Japanese Application Serial No. 2016-502344, Notification of Reasons for Rejection dated Apr. 11, 2017", w/ English Translation, 6 pgs.
"Japanese Application Serial No. 2016-502344, Notification of Reasons for Rejection dated Nov. 1, 2016", w/ English Translation, 10 pgs.
"Japanese Application Serial No. 2016-502344, Response filed Mar. 30, 2017 to Notification of Reasons for Rejection dated Nov. 1, 2016", with English translation of claims, 12 pgs.
"Japanese Application Serial No. 2016-502344, Response filed Jul. 10, 2017 to Notification of Reasons for Rejection dated Apr. 11, 2017", w/ English Translation, 8 pgs.
"Japanese Application Serial No. 2018-094142, Examiners Decision of Final Refusal dated Jan. 7, 2020", W/ English Translation, 6 pgs.
"Japanese Application Serial No. 2018-094142, Notification of Reasons for Rejection dated May 21, 2019", W/English Translation, 6 pgs.
"Japanese Application Serial No. 2018-094142, Response filed Aug. 8, 2019 to Notification of Reasons for Rejection dated May 21, 2019", with English translation of claims, 6 pgs.
Batchelor, Kester, et al., "Electrosurgical Instrument", Potentially related U.S. Appl. No. 14/178,411, filed Feb. 12, 2014, 24 pgs.
Japanese Office Action dated May 21, 2019, Application No. JP2018094142.
"U.S. Appl. No. 14/589,482, Final Office Action dated Sep. 15, 2020", 14 pgs.
"U.S. Appl. No. 14/589,482, Response filed Dec. 15, 2020 to Final Office Action dated Sep. 15, 2020", 16 pgs.
"U.S. Appl. No. 14/589,515, Notice of Allowance dated Aug. 20, 2020", 5 pgs.
"U.S. Appl. No. 14/589,515, Supplemental Notice of Allowability dated Nov. 30, 2020", 2 pgs.
"Brazilian Application Serial No. 112015018395.6, Office Action dated Aug. 18, 2020", with machine translation.
"Brazilian Application Serial No. 112015018395.6, Response filed Nov. 13, 2020 to Office Action dated Jun. 21, 2020", with machine translation, 239 pgs.
"Chinese Application Serial No. 201810113314.0, Response filed Aug. 20, 2020 to Office Action dated Apr. 10, 2020", with English translation of claims, 14 pgs.
"Indian Application Serial No. 4991/CHENP/2015, Office Action dated Nov. 23, 2020", with English claims, 6 pgs.
"U.S. Appl. No. 14/589,482, Notice of Allowance dated Sep. 17, 2021", 8 pgs.
"U.S. Appl. No. 16/048,553, Non Final Office Action dated Feb. 10, 2022", 11 pgs.
"U.S. Appl. No. 16/048,553, Examiner Interview Summary dated Apr. 4, 2022", 2 pgs.
"U.S. Appl. No. 16/048,553, Response filed May 10, 2022 to Non Final Office Action dated Feb. 10, 2022", 11 pgs.

(56) References Cited

OTHER PUBLICATIONS

"U.S. Appl. No. 16/395,142, Non Final Office Action dated Apr. 29, 2022", 12 pgs.

"U.S. Appl. No. 16/048,553, Non Final Office Action dated Aug. 16, 2022", 14 pgs.

"U.S. Appl. No. 16/395,142, Final Office Action dated Aug. 22, 2022", 11 pgs.

"U.S. Appl. No. 16/395,142, Response filed Jul. 29, 2022 to Non Final Office Action dated Apr. 29, 2022", 15 pgs.

"U.S. Appl. No. 16/048,553, Examiner Interview Summary dated Nov. 4, 2022", 2 pgs.

"U.S. Appl. No. 16/395,142, Response filed Oct. 18, 2022 to Final Office Action dated Aug. 22, 2022", 14 pgs.

"U.S. Appl. No. 16/048,553, Response filed Nov. 16, 2022 to Non Final Office Action dated Aug. 16, 2022", 11 pgs.

"U.S. Appl. No. 16/395,142, Non Final Office Action dated Feb. 1, 2023", 11 pgs.

"Brazilian Application Serial No. 122015018776.1, Opinion for non-patenteability (RPI 7.1) dated Oct. 25, 2022", with machine translation, 6 pgs.

"U.S. Appl. No. 16/048,553, Notice of Allowance dated Apr. 26, 2023", 5 pgs.

"U.S. Appl. No. 16/048,553, Supplemental Notice of Allowability dated Jan. 19, 2023", 2 pgs.

"U.S. Appl. No. 16/395,142, Advisory Action dated Oct. 28, 2022", 3 pgs.

"U.S. Appl. No. 16/395,142, Corrected Notice of Allowability dated Aug. 11, 2023", 3 pgs.

"U.S. Appl. No. 16/395,142, Notice of Allowance dated May 31, 2023", 6 pgs.

"U.S. Appl. No. 16/395,142, Response filed May 1, 2023 to Non Final Office Action dated Feb. 1, 2023", 14 pgs.

"U.S. Appl. No. 18/358,448, Preliminary Amendment filed Nov. 10, 2023", 7 pgs.

* cited by examiner

ELECTROSURGICAL INSTRUMENT

CROSS-REFERENCE TO RELATED APPLICATIONS

This application is a Continuation of U.S. patent application Ser. No. 14/178,411, filed Feb. 12, 2014 and now issued as U.S. Pat. No. 10,292,757, which claims the benefit of priority to U.S. Provisional Patent Application No. 61/902,933, filed Nov. 12, 2013 and U.S. Provisional Patent Application No. 61/787,731, filed Mar. 15, 2013; the contents of which are incorporated herein by reference in their entireties.

FIELD

The present teachings generally relate to electrosurgical instrument tip arrangements for use in both bipolar and combination monopolar/bipolar devices. More specifically, the present teachings address the arrangement of multi-electrode electrosurgical tip designs.

BACKGROUND

Typically, electrosurgical instruments have stand-alone monopolar capabilities or bipolar capabilities. Combination devices that can be utilized in both monopolar and bipolar mode have also been developed. Based upon the operational needs of each type of device, different electrosurgical device tip designs are generally utilized for each of stand-alone monopolar, bipolar, or combination monopolar/bipolar devices.

Some examples of such electrosurgical instrument tip arrangements may be found in U.S. Pat. Nos. 5,403,312; 6,030,384; 6,113,596; 6,458,128; 6,926,716; and 7,604,635, all of which are incorporated by reference herein for all purposes. It would be desirable to have an electrosurgical device tip design that provides improved function for a stand-alone bipolar device and may also be utilized for a combination monopolar/bipolar device. It would be further beneficial to have an electrosurgical device that may be used in open surgery as forceps and may be used for electrical cutting and/or hemostasis.

SUMMARY

The present teachings meet one or more of the needs identified herein by providing an electrosurgical instrument comprising a first arm carrying a first and second electrode and an optional third electrode, wherein the first and second electrode are optionally two integrally formed discrete conductors. The instrument may further include a second arm opposing the first arm, the second arm carrying one of a nonconductor element or one or more conductive elements. Only one of the first electrode, second electrode, third electrode, or one or more conductive elements may pass energy in a monopolar mode and at least two of the first electrode, second electrode, or one or more conductive elements may pass energy in a bipolar mode.

In another embodiment of the present teachings, the instrument may comprise a first arm carrying a first and second electrode and an optional third electrode and a second arm opposing the first arm, the second arm carrying one or more electrodes. The first arm, the second arm or both may include a plurality of electrodes free of direct contact with one another but in electrical connectivity with one another to pass energy in a monopolar mode and at least two of the first electrode, second electrode, or one or more electrodes of the second arm pass energy in a bipolar mode.

Another possible embodiment of the present teachings comprises an electrosurgical instrument comprising a first arm carrying a first and second electrode and a second arm opposing the first arm, the second arm carrying a conductive element. The conductive element may be a floating electrode so that a preferential path is created for energy flow from one or more of the first and second electrode via the floating electrode in bipolar mode.

Yet another embodiment addressed by the present teachings includes an electrosurgical instrument comprising a first arm carrying a first electrode and a second arm opposing the first arm, the second arm carrying a second electrode. Only one of the first electrode or second electrode may pass energy in a monopolar mode and both of the first electrode and second electrode may pass energy in a bipolar mode.

Another embodiment addressed by the teachings herein includes an electrosurgical instrument comprising a first arm carrying a first electrode and a second arm opposing the first arm, the second arm carrying a second electrode. At least a portion of one or more of the first electrode and second electrode may pass energy in a monopolar mode and at least a portion of one or more of the first electrode and second electrode may pass energy in a bipolar mode. At least a portion of one or more of the first electrode and second electrode passes energy in monopolar mode and extends from a spine or side edge of at least one of the first or second arms.

The teachings herein further provide for an electrosurgical instrument comprising a first arm carrying a first electrode, a second arm opposing the first arm, the second arm carrying a second electrode, a third electrode, and optionally one or more additional electrodes. The first electrode and second electrode may pass energy in a monopolar mode and at least two of the first electrode, third electrode, or one or more additional electrodes may pass energy in a bipolar mode.

The teachings herein provide for electrosurgical instrument tip arrangements that may be utilized in both bipolar and combination monopolar/bipolar devices. The teachings herein further provide for electrosurgical instrument tip arrangements that may be used in open surgery as forceps and may be used for electrical cutting and/or hemostasis. The teachings herein also provide for tip arrangements including a plurality of electrodes and insulating portions for facilitating improved energy flow depending upon the need for cutting or hemostasis and the monopolar or bipolar nature of the energy facilitated through the tips.

DETAILED DESCRIPTION

Figure 3:
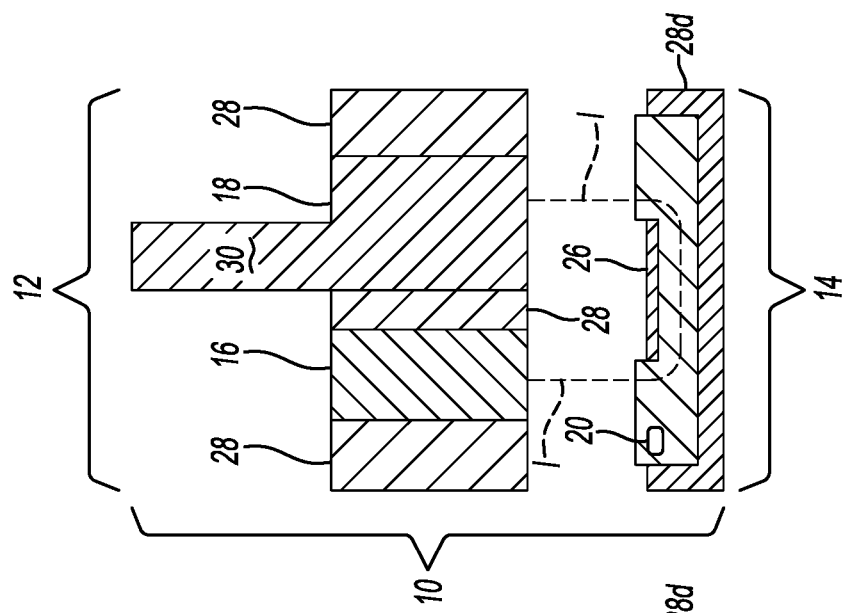
FIG. 3 shows an additional illustrative example of a tip arrangement of an electrosurgical instrument in accordance with the present teachings.

This application claims the benefit of the filing date of U.S. Provisional Application Ser. No. 61/787,731 filed Mar. 15, 2013, and U.S. Provisional Application No. 61/902,933, filed Nov. 12, 2013 the contents of these applications being hereby incorporated by reference for all purposes.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings are directed toward electrosurgical instrument tip arrangements. The tips are generally those associated with electrosurgical forceps. The electrosurgical instruments upon which the tips are located may be any device that may be used by a surgeon to perform a surgical procedure. The electrosurgical device may be used to cut, perform hemostasis, coagulate, desiccate, fulgurate, electrocauterize, or any combination thereof. The electrosurgical instrument tips may be integrated with any device that includes bipolar capabilities or both bipolar capabilities and monopolar capabilities. The electrosurgical instrument tips are preferably utilized in either open or laparoscopic surgery as opposed to solely laparoscopic procedures.

The instrument tips may be utilized in combination monopolar/bipolar devices. When in a monopolar configuration (e.g., when included in a combination monopolar/bipolar device) one or more of the plurality of electrodes may receive power through the device and a return electrode may be located at another location outside of any hand-held portion of the electrosurgical instrument. Alternatively, two or more electrodes may be integrally formed or in electrical connectivity with one another to function as monopolar electrode. A monopolar configuration may be desired to cut tissue, apply power to a large area, or a combination thereof. Any use of the instrument tips described herein in monopolar mode may be for the purpose of dissection, less delicate procedures, less localized electrosurgery, or both when compared to bipolar electrosurgery.

The instrument tip when in a bipolar configuration (e.g., as part of a stand-alone bipolar device or as part of a combination monopolar/bipolar device) may be arranged such that one of a plurality of electrodes receives power and that power transfers to a second adjacent and/or opposing electrode creating a path for the power that is relatively short when compared to the path in the monopolar configuration. In a preferred bipolar configuration, the instrument tip may include two electrodes on a first surface and one electrode (e.g., one conductive portion) on an opposing second surface. In yet another preferred bipolar configuration, the instrument tip may include a first bipolar electrode on a first surface and a second bipolar electrode on a second opposing surface. The surfaces may be configured as forceps including first and second arms such that a first arm carries the first surface and a second arm carries the second surface. One or more electrodes or any other conductive portion may be located in opposing relationship with one or more additional electrodes or conductive portions. One or more electrodes may be located on non-opposing (e.g., outside edge) surfaces of the arms of the instrument tip. It is understood that conductive portions may be electrodes or may simply be conductive in nature and not operating as an electrode.

The instrument tips may be forceps instrument tips. The forceps may be any forceps that may be used to grip, hold, squeeze, or a combination thereof one or more objects. The forceps may include one or more finger grips (i.e., configured like scissors) that may be used to move the forceps so that they may be used to grip one or more objects. The forceps may be free of finger grips and be actuated by direct pressure being applied to opposing sides of the forceps so that the forceps close and grip an object. The forceps include the first and second arms.

Each arm may include one or more surfaces that form the instrument tip arrangements described herein. As mentioned above, the instrument tips may be configured in one or more electrosurgical configurations (e.g., a monopolar configuration, bipolar configuration, or a combination of both). In addition to the arrangement of the tip surfaces as described herein, the tips may include teeth, serrations, mouse teeth, free of teeth (i.e., smooth), or any combination thereof. The instrument tips may include a plurality of conductive portions which may include one or more electrodes and one or more insulating portions. Preferably, the tip region includes insulation on the non-contact portions of the arms so that electrosurgical energy is not transferred through incidental contact. The arms may include an active portion (e.g., a conductive portion) and an inactive portion (e.g., an insulated portion).

The active portion may be any portion of the device that may be used to apply power or facilitate the flow of energy. The active portion may be the same portion as the electrodes on the surfaces of the arms. Thus, for example, when tissue is grasped between the first and second surfaces (e.g., contact portions) of the arms, power may be supplied to the tissue through this contact portion. Energy may thus flow through one or more of the first and second surfaces and into and/or onto the tissue. The active portions may be substantially surrounded by inactive portions or portions that are insulated. The inactive portion may be any portion that does not supply power, that is insulated, or both. The inactive portion may be any portion that may transfer power through incidental contact. For example, an outside portion of the arms may be coated with an insulating material so that if the arms accidentally contact tissue proximate to the tissue of interest the proximate tissue is not subjected to a transfer of power. The inactive portion and the active portion may be made of different materials, coated with different materials, or both.

The arms may be made of any material that may be used to grip, hold, squeeze, or a combination thereof and provide monopolar power, bipolar power, or a combination of both to a desired location. The arms may be made of one material and at least a portion of the tip region of each arm may include or be coated with one or more materials that may be insulating. At least a portion of the tip region of one or both of the arms may include a conductive material. The conductive material may be formed as a coating having a higher conductivity than a base material. The conductivity of a given portion of the arm may have a higher or lower conductivity than an adjacent portion of the arm. The one or more arms may include one or more materials along the length of the arm. For example, the arms may be entirely made of stainless steel. Preferably, each arm includes two or more materials. For example, the arms may have a base material of stainless steel and at least a portion of the arms may be coated with an insulating material such as silicone or polytetrafluoroethylene (PTFE). The arms may include any material that is safe for use in a surgical procedure, and preferably an electrosurgical procedure. The arms may include metals, plastics, polymers, elastomers, gold, silver, copper, titanium, aluminum, iron based metals, stainless steel, silicone, polytetrafluoroethylene (PTFE), insulating polymers, rubber, or a combination thereof. Preferably, each arm is substantially coated with an insulating material except for a contact region where an arm directly contacts a second arm. The arms may be coated in regions where the user contacts the arms. The arms may have an active portion and a passive portion. For example, the active portion may be a metal that extends through the arms and is used to provide monopolar energy, bipolar energy, gripping capabilities, holding capabilities, squeezing capabilities, or a combination thereof. The passive portion may be a portion that houses the active portion. The passive portion may be a housing.

The arms may be located within a housing. The housing may be any device that may include one or more arms and be gripped by a user during use. The housing may provide for electrical connection, mechanical connection or a combination thereof between two or more arms. The housing may be a pivot point so that the two arms may be moved when the housing is compressed. The housing may substantially surround the arms so that only the tip region including the tip portions extends out of the housing and is exposed. The housing may surround an outer surface of the arms and an inner surface of the arms may be exposed. The housing may be electrically connected to a power source and provide power to each of the arms. The housing may be electrically insulating. The housing may include one or more activation buttons, one or more printed circuit boards and associated controls, one or more monopolar electrodes, one or more bipolar electrodes, one or more shields, one or more channels, or a combination thereof.

The monopolar electrode may be any device that may be used to apply monopolar power during a procedure. The monopolar electrode may be a separate piece that when activated may be used to supply monopolar power. A monopolar electrode may be formed on only one arm. A monopolar electrode may be formed on both arms. The monopolar electrode may be located on or adjacent an inner edge surface of an arm of the device. The monopolar electrode may be located on or adjacent an outer edge surface of the arm of the device. The monopolar electrode may operate in monopolar mode upon receiving monopolar energy. A portion of the monopolar electrode may also operate as part of a bipolar electrode system. The monopolar electrode may be located on one surface of one arm along with a second electrode. The monopolar electrode may be used for electrically cutting.

One or more of the electrodes (e.g., the first, second, third, fourth or any additional electrode) may be made of the same material as one or both of the arms. Preferably, the arms and the one or more electrodes are made of different materials. The one or more electrodes may be made of one material. Preferably, the one or more electrodes include two or more materials. The one or more electrodes may be formed of two or more integrally formed electrodes (e.g., discrete conductors) having a joint formed therebetween. In one embodiment, one of the two integrally formed electrodes may allow for better thermal dissipation while the other allows for reduced thermal dissipation. The one or more electrodes may be made of stainless steel, copper, silver, titanium, a metal, a surgical steel, a metal with good thermal dissipation properties, a metal with reduced thermal dissipation properties, or a combination thereof. The one or more electrodes (or a portion thereof) may include a coating. The coating may be any coating that provides insulating properties, provides improved thermal dissipation, prevents corrosion, or a combination thereof. The coating may be a polymer, an elastomer, silicone, polytetrafluoroethylene (PTFE), the like, or a combination thereof. The coating may extend over substantially the entirety of the one or more electrodes except for the active region of the one or more electrodes. The one or more electrodes may include one or more electrode insulators.

Any electrode insulator may be formed of a material that may insulate all or a portion of the active portions of the arms. The electrode insulator may prevent undesired contact of tissue with the electrode when the electrosurgical device is in use. The electrode insulator may prevent power from being transferred from one or both of the arms to the one or more electrodes.

A first electrode may be located on a first surface which is formed on the first arm. The first electrode may be located along an inner surface of the first arm. The first electrode may extend from one or more outside surfaces of the first arm. The first electrode (or any of the electrodes) may be located along the inner surface of the first arm and may also extend from an outside surface of the first arm. The first arm and first surface may include a first and second electrode. The second electrode may extend from an outside surface of the first arm. The second electrode (or any of the electrodes) may be located along the inner surface of the first arm and may also extend from an outside surface of the first arm. The second electrode may be substantially free of any direct contact (e.g., direct physical contact as opposed electrical contact) with the first electrode. The first and second electrodes (or any combination of electrodes) may be integrally formed discrete conductors which may have a joint formed therebetween. The first and second electrodes (or any combination of electrodes) may be in electrical communication with one another for operating together as an electrode. One or more of the first and second electrode may be a bipolar electrode. One or more of the first and second electrode may be a monopolar electrode. One or more of the first and second electrode may function as both a monopolar electrode and a bipolar electrode. The first and second electrodes may be located adjacent each other for forming the first surface. The first arm may also include a third electrode, which may also be located on the first surface of the first arm or may extend from an outside edge of the first arm. The third electrode may be adapted for operation in monopolar mode only, bipolar mode only, or may be adapted for both monopolar and bipolar use. Any of the first, second or third electrodes may include an insulating portion located adjacent one or more terminal edges of the electrode, whereby such insulating portion is located in between one or more electrodes. The size of the insulating portion between the one or more electrodes (e.g., the distance between the one or more electrodes) must be sufficiently large to prevent direct contact between the one or more electrodes. The size of the insulating portion between the one or more electrodes may be small enough so that power can flow from one electrode to another electrode, generally via a portion of tissue.

A second surface may oppose the first surface and may be located on the second arm. The second surface may include one or more conductive elements which may be an electrode. The second surface may also include an insulating portion. The insulating portion may be located adjacent the conductive element on at least one edge of the conductive element. The insulating portion may be located along at least two edges of the conductive element. The insulating portion may be located along at least three edges of the conductive element. Alternatively, the second surface may be substantially free of any conductive element. The second surface may consist essentially of an insulating portion. The conductive element on the second surface may be an electrode located along the inner surface of the second arm and may oppose one or more electrodes on the inner surface of the first arm. The conductive element may be an electrode located along an outside edge of the second arm. Two or more conductive elements may be located along the inner surface of the second arm and may also extend from an outside surface of the second arm. The conductive element may be an electrode that is adapted for operation in monopolar mode, bipolar mode, or both monopolar and bipolar mode.

The first arm may include a first electrode, which may operate in monopolar mode, bipolar mode, or both monopolar and bipolar mode. The first electrode may be located along an inner surface of the first arm, but a portion of the first electrode may also extend from one or more side edges of the arm or even a back edge (e.g., spine portion) of the arm. The first electrode may extend from multiple side edges of the first arm. The second arm may include a second electrode and energy may pass from the first electrode on the first arm to a second electrode on the second arm when used in bipolar mode. In the same arrangement, a switch may be activated so that only the first electrode passes energy when in monopolar mode (or alternatively only the second electrode passes energy in monopolar mode). The first arm may include a first electrode and the second arm may include an opposing second electrode such that both of the first and second electrodes are located along an inner surface portion of each of the first and second arms and both of the first and second electrodes include an extension portion extending from a side edge or back edge of each of the first arm and second arm. Energy may pass from the first electrode to the second electrode in bipolar mode. Each of the extension portions may pass energy in monopolar mode.

The first arm may include a first and second electrode. One or more of the first and second electrodes may operate in bipolar mode. One or more of the first and second electrodes may operate in monopolar mode. One or more of the first and second electrodes may operate in both bipolar and monopolar mode. The second arm may include only insulating material and may be substantially free of any conductive portion (e.g., electrode). The second arm may include one or more electrodes. The second arm may include a first and second electrode. The first arm may include a third electrode. The second arm may include a third electrode. Any electrode located on the first or second arm may be located on an inner surface of the arm or may be located (e.g., may extend from) an exterior surface of the arm which may be a side edge of the arm or a back edge (e.g., a spine portion) of the arm.

Any electrode may be formed of one material or of two or more materials. Two or more electrodes of the same or different material may also be integrally formed as two discrete conductors to act as a single electrode. The two or more materials may be selected based upon desired thermal dissipation of the electrode at different locations. As an example, a low thermal dissipation material may be utilized for the electrode through which energy flows during use of the device in monopolar mode. Such material would allow that portion of the electrode to heat thereby requiring less overall voltage. A high thermal dissipation material may be utilized for a second electrode. The two discrete conductors (low dissipation and high dissipation) may include a joint located therebetween. The joint may provide a thermal insulation function such that the heating of the lower thermal dissipation material does not cause heating of the high thermal dissipation material. In one non-limiting example, the lower thermal dissipation material may include steel and the high thermal dissipation material may include copper and/or silver.

The concept of a joint between two or more electrodes in an effort to control heat and electricity transfer may also be utilized in electrodes formed of only one monolithic material. Such a joint may be formed by the shaping of the conductive materials. More specifically, one or more electrodes may be formed to have a "bottle-neck" feature where the material for forming the electrode is indented and adjacent to two or more lobes (see for example FIGS. 26a and 26b). This indentation allows for thermal separation by allowing energy transfer but minimizing heat transfer between lobes. The joint may be in the form of a wave shaped ribbon which may be pressed into slot located along the tip. The joint may be formed as flat ribbon pressed into a slot with knobs. The slot along the tip may be filled with epoxy, putty, or filler to hold the ribbon in place.

In one embodiment, in the event that the conductive element is a floating electrode, the interaction between the first and second bipolar electrodes located along the inner surface of the first arm and the floating electrode may be such that energy flows through the first bipolar electrode, towards the floating electrode and back to the second bipolar electrode. During use, a tissue portion may be located between the first and second inner surfaces (e.g., between the first and second arms). Thus, energy may flow through the first bipolar electrode and then flow to any combination of onto the tissue, into the tissue, or through the tissue. If the instrument receives a tissue in between the first and second arm during use in bipolar mode, bipolar energy travels through at least a portion of the tissue when moving along an energy path between the first electrode, the floating electrode, and the second electrode. The second arm may include an insulation portion (as shown for example in FIG. 4b) so that bipolar energy travels through a larger portion of the tissue as compared to that of a second arm without the insulation portion.

A first and second electrode may be located on the first of two opposing arms and a third electrode may be located on the second of the two opposing arms. Alternatively, a first, second, and third electrode may be located on the first arm. A first electrode may be located on the first arm and a second electrode located on the second arm. Thus, tissue located in between the two opposing arms may electrically connect the arms, form an electrical bridge between the two arms, or both. In the event that the device is utilized in monopolar mode, the first arm may have a single monopolar electrode (which may be the first, second, or third electrode) and the tissue contacted by that electrode may electrically connect the monopolar electrode with a return electrode, act as an electrical bridge between the monopolar electrode and the return electrode, or both. One or more of the electrodes may be combined to form a single potential in monopolar mode. In the event that the device is a combination monopolar/bipolar device, the circuit may include a switch that switches between the monopolar configuration and the bipolar configuration. The switch may activate one of the bipolar electrodes and deactivate the return pad or vice versa, activate one bipolar electrode and deactivate the monopolar electrode or vice versa, deactivate one bipolar electrode and leave the electrode open (i.e., not powered), deactivate the monopolar electrode and leave the electrode open, deactivate both bipolar electrodes and activate the monopolar electrode and the return electrode or vice versa, or a combination thereof. The monopolar electrode (e.g., one of the first and second electrode), one or more of the bipolar electrodes (e.g., the first and second electrode), or a combination thereof may be connected to an alternating current power source, a direct current power source, or both. Preferably, the monopolar electrodes, the bipolar electrodes, or both are connected to an alternating current power source. The monopolar electrode, the bipolar electrodes, or both may complete a circuit when in contact with tissue.

The device tip arrangements as described herein are designed for improved function and interchangeability in a variety of device configurations. Each surface described may include specific materials having desired functions at selected locations to improve the function of the device. Such materials may be selected and located depending on the desired function of the device. For example, the second arm may carry a nonconductor element and be substantially free of any conductive surface, such that only the first arm includes conductive elements. Thus, the second arm may be free of any electrical connectivity and merely provides a compressive force during a surgical procedure. Alternatively, the second arm carries a conductive element. The conductive element on the second arm may act to improve the path of energy between the electrodes in bipolar mode. The conductive element may be a floating electrode so that a preferential path is created for energy flow from one or more of the first and second electrode and the location of the path is easily modified by location of the floating electrode. Thus the energy may flow between the first electrode to the second electrode via the floating electrode in bipolar mode. The energy may flow from only one of the first or second electrode to a return electrode remote from but in electrical communication with the first arm in monopolar mode.

One or more of the first and second arms may include insulated portions. The second arm may carry an insulation portion. This insulation portion may be located so that it extends the length of an energy path between the first and second electrode (see length (I) at FIGS. 2 and 3). The first arm may include an insulation portion between the first and second electrodes. The second arm may include an insulation portion that opposes the insulation portion between the first and second electrodes on the first arm.

Figure 1:
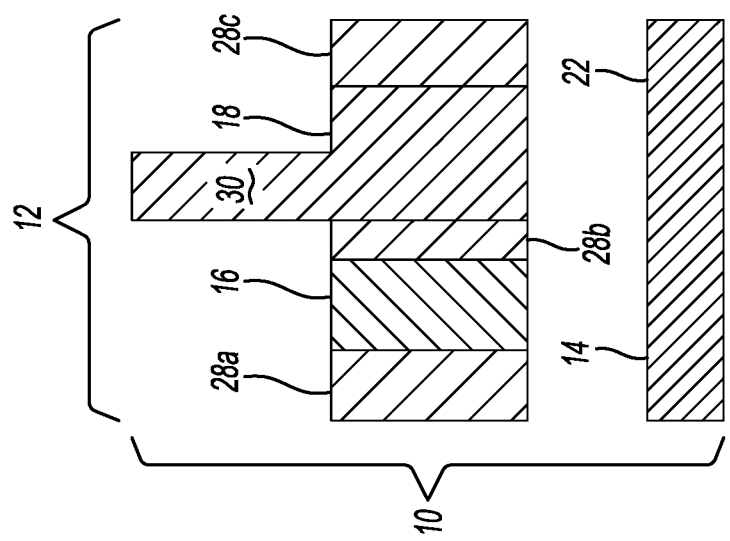
FIG. 1 shows an illustrative example of a tip arrangement of an electrosurgical instrument in accordance with the present teachings.

FIG. 1 shows an illustrative arrangement for an electrosurgical instrument tip 10. The tip 10 includes a first arm 12 and a second arm 14. The first arm 12 includes a first electrode 16. The first arm also includes a second electrode 18. The second arm 14 may be free of any electrode and may have only a non-conductive component 22 and no conductive component. The first arm 12 may also include insulating (non-conductive) portions 28a, 28b, and 28c, such that a first insulating portion 28a is located adjacent a terminating edge of the first electrode. A second insulating portion 28b may be located in between the first electrode and second electrode. A third insulating portion 28c may be located adjacent a terminating edge of the second electrode.

Figure 2:
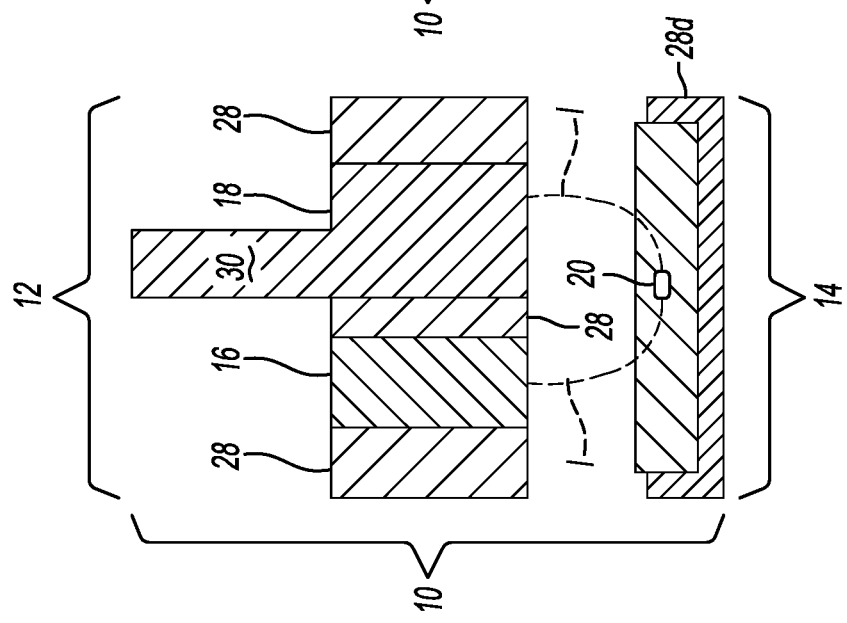
FIG. 2 shows an additional illustrative example of a tip arrangement of an electrosurgical instrument in accordance with the present teachings.

Alternatively, as shown in FIG. 2, the instrument tip 10 includes a first arm 12 and a second arm 14. The first arm 12 includes a first electrode 16. The first arm also includes a second electrode 18. The second arm 14 also includes an electrode 20 (e.g., a third electrode) which may be a floating electrode (e.g., may be free of any electrical connection with any electrode or ground) or may be fixed at one potential (e.g., electrically attached to the ground). The second arm may include one or more insulating (non-conductive) portions 28. The second arm includes a first insulating portion 28d which substantially surrounds the electrode 20 (e.g., the conductive portion) on the second arm on at least one, two, or three sides. The electrode 20 may instead be coplanar with the first insulating portion 28d or may extend beyond the surface of the first insulating portion. As in the embodiment shown at FIG. 1, The first arm 12 may also include insulating (non-conductive) portions 28a, 28b, and 28c, such that a first insulating portion 28a is located adjacent a terminating edge of the first electrode. A second insulating portion 28b may be located in between the first electrode and second electrode. A third insulating portion 28c may be located adjacent a terminating edge of the second electrode.

FIG. 3 illustrates an additional embodiment including a second insulating portion 26 located on the second arm. The addition of the second insulating portion 26 assists in directing energy from the first electrode 16 to the second electrode 18 via the third electrode 20 such that the flow of energy runs between the second insulating portion 26 and first insulating portion 28d of the second arm.

Figure 4A:
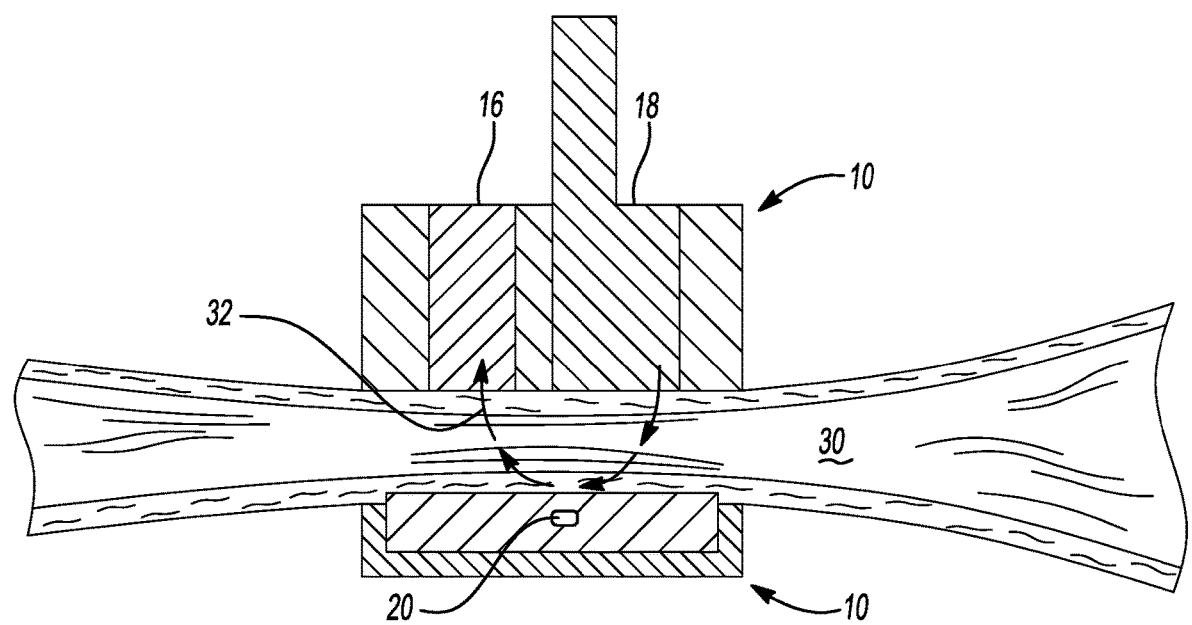
FIG. 4*a* shows a cross-sectional view of the tip arrangement of FIG. 2 when contacting a tissue sample.

FIG. 4a depicts a cross-sectional view of an interface between the instrument tip 10 of FIG. 2 and a tissue sample 30. As shown, the path of energy 32 flows into the second electrode 18, through a portion of the tissue 30 toward the third electrode 20 and back to the first electrode 16.

Figure 4B:
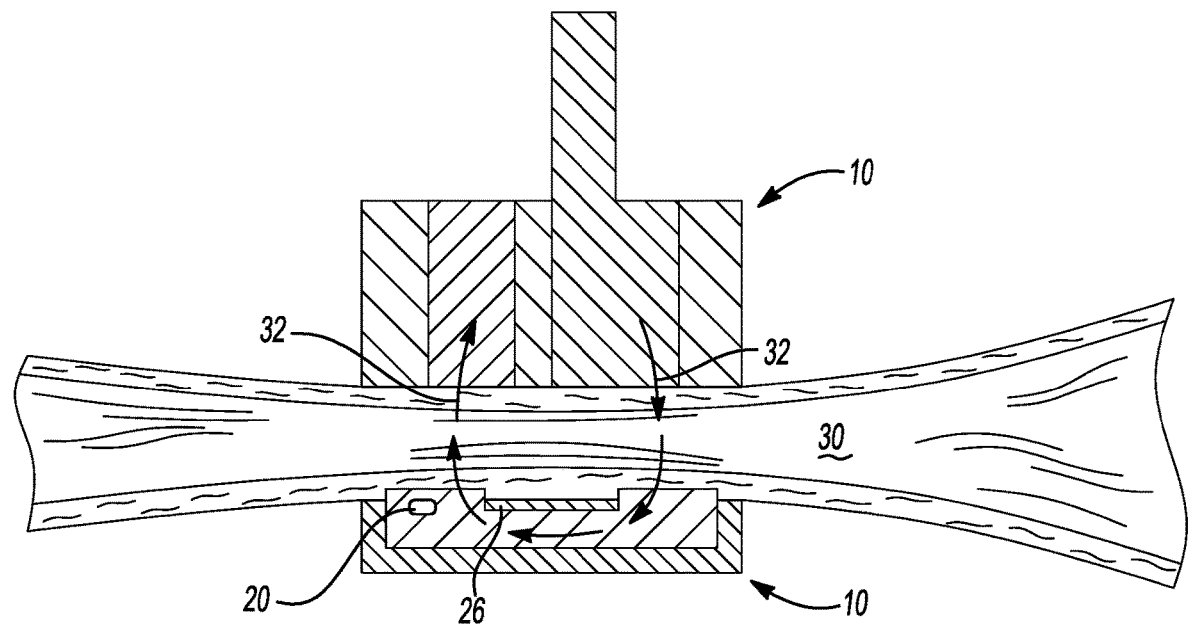
FIG. 4*b* shows a cross-sectional view of the tip arrangement of FIG. 3 when contacting a tissue sample.

FIG. 4b depicts an additional cross-sectional view of an interface between the instrument tip 10 of FIG. 3 and a tissue sample 30. In this embodiment, the inclusion of the second insulating portion 26 causes the path of energy 32 to extend further into the tissue 30 as the second insulating portion acts to guide the energy further toward the third electrode 20. The length of the second insulating portion 26 is also shown as longer than the length of the opposing insulating portion 28b, thus further extending the path of energy 32.

Figure 5A:
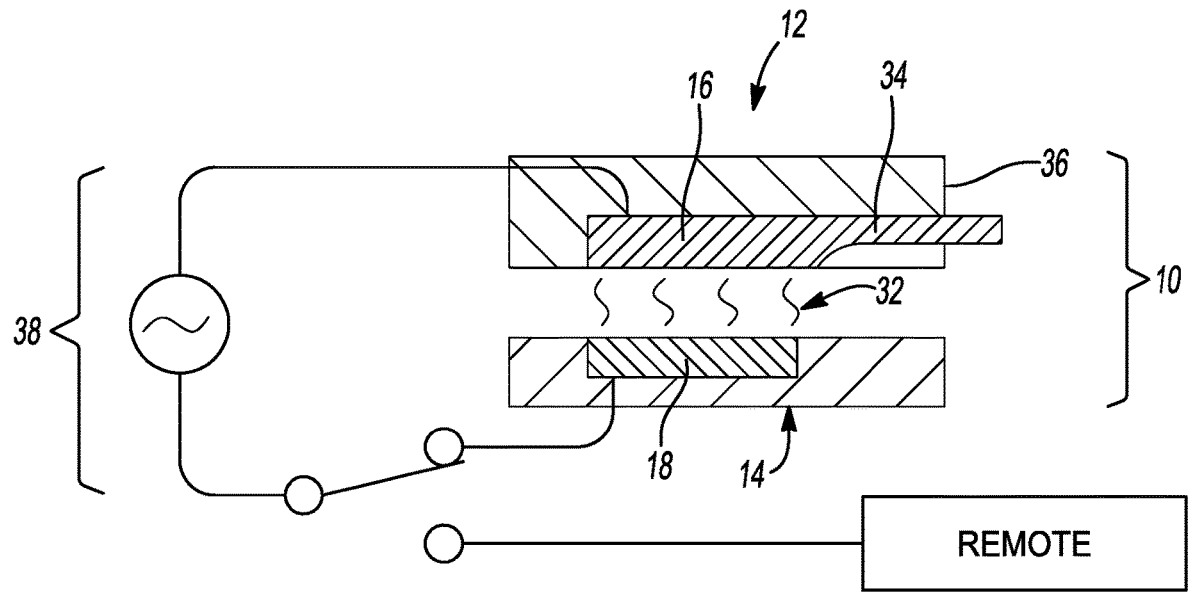
FIG. 5*a* shows an illustrative example of a tip arrangement and electrical circuit of an electrosurgical instrument in accordance with the present teachings.

FIG. 5a displays an instrument tip 10 and associated electrical connections in use in bipolar mode. The first arm 12 includes a first electrode 16 and the second arm 14 includes a second electrode 18. A first extension portion 34 of the first electrode 16 extends from a side edge 36 of the first arm. When used in bipolar mode, the path of energy 32 moves between the first electrode and second electrode. The first and second electrodes are further connected via a circuit 38.

Figure 5B:
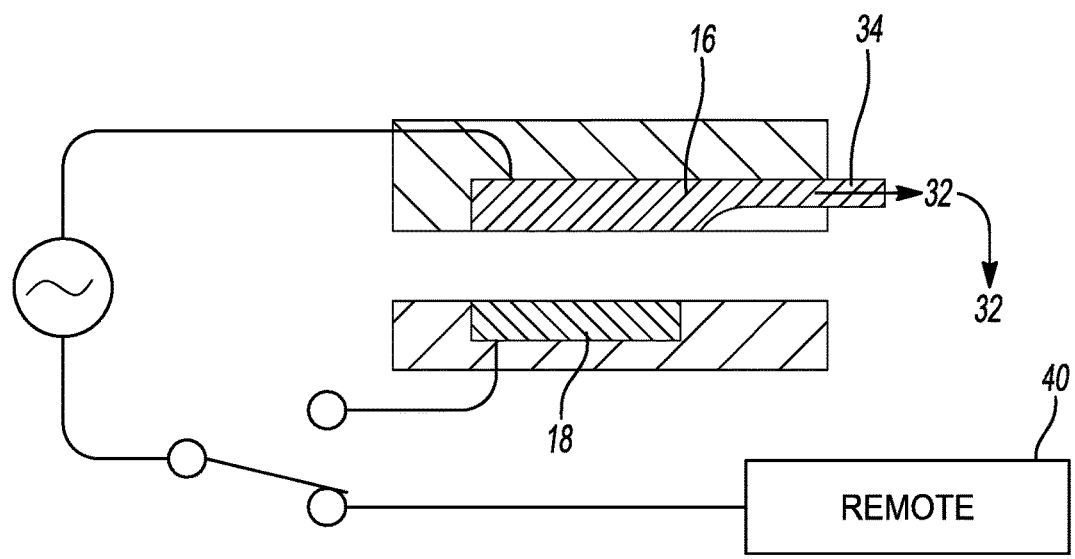
FIG. 5b shows an additional illustrative example of a tip arrangement and electrical circuit of an electrosurgical instrument in accordance with the present teachings.

FIG. 5b shows the instrument tip of FIG. 5a in use in monopolar mode. The first and second electrodes (16, 18) are present, however there is no energy flow between the first and second electrode. The path of energy 32 flows instead through the extension portion 34 of the first electrode, through tissue (not shown), to a remote ground pad 40.

Figure 6A:
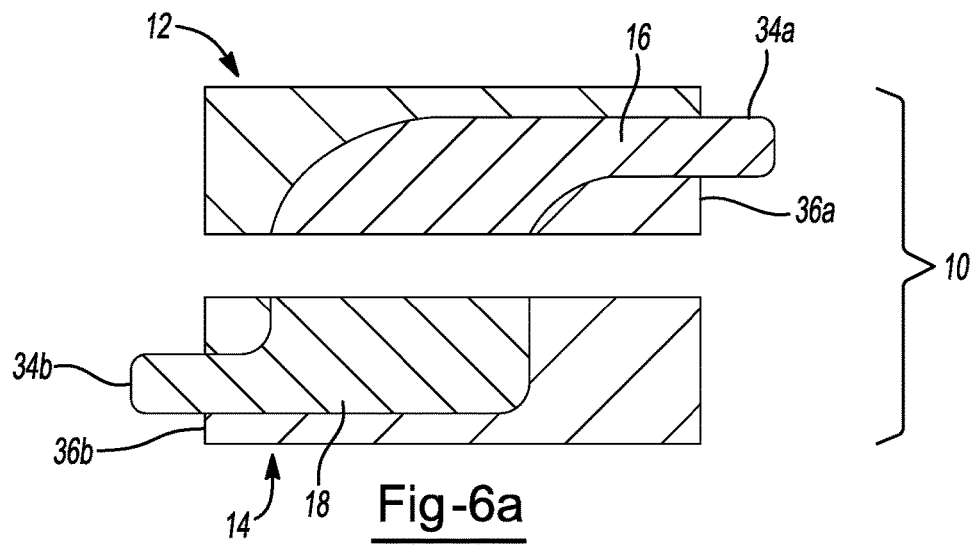
FIG. 6a shows an additional illustrative example of a tip arrangement of an electrosurgical instrument in accordance with the present teachings.

FIG. 6a shows an instrument tip 10 including a first electrode 16 on the first arm 12 and a second electrode 18 on the second arm 14. Both of the first and second electrodes include an extension portion 34a, 34b extending from a terminating side edge 36a, 36b of the first arm and second arm respectively. In such an arrangement both the first and second electrodes have the capability of operating in monopolar mode.

Figure 6B:
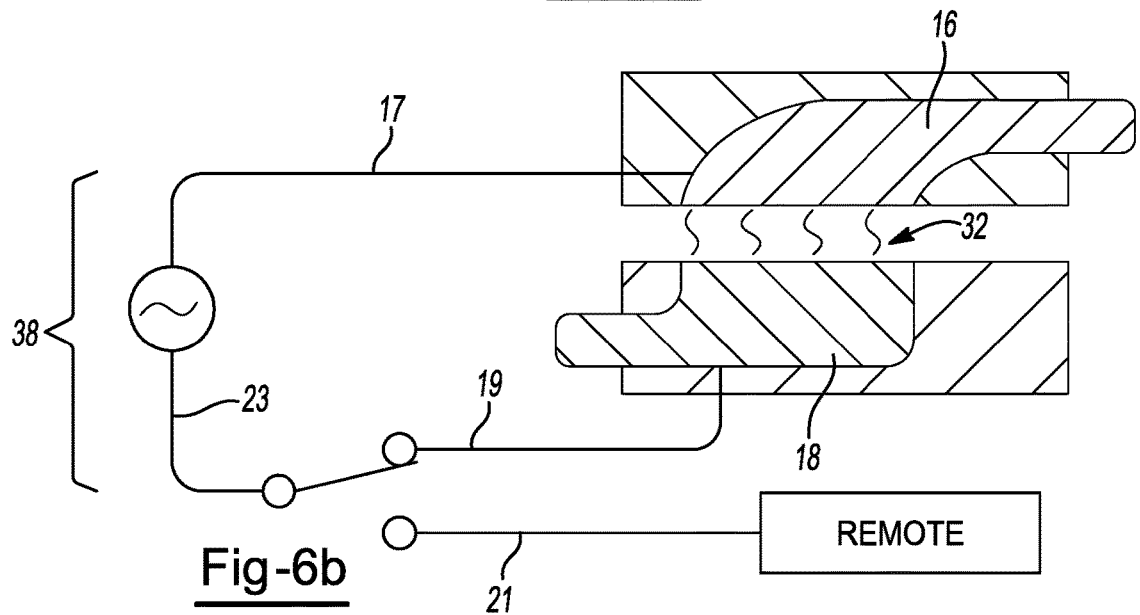
FIG. 6b shows an additional illustrative example of a tip arrangement and electrical circuit of an electrosurgical instrument in accordance with the present teachings.

As shown in FIG. 6b, the instrument tip of FIG. 6a may be connected via a circuit 38. When used in bipolar mode, the energy path 32 flows between the first electrode 16 and second electrode 18 and the first and second electrode are connected to an energy source (and one another) via the circuit 38. The first electrode 16 is connected to a power source via a first connector 17, and the second electrode 18 is connected to a power source via a second connector (e.g., a second connector that includes connector portions 19 and 23). A third connector 21 is available, but does not provide connectivity when the device is used in bipolar mode.

Figure 6C:
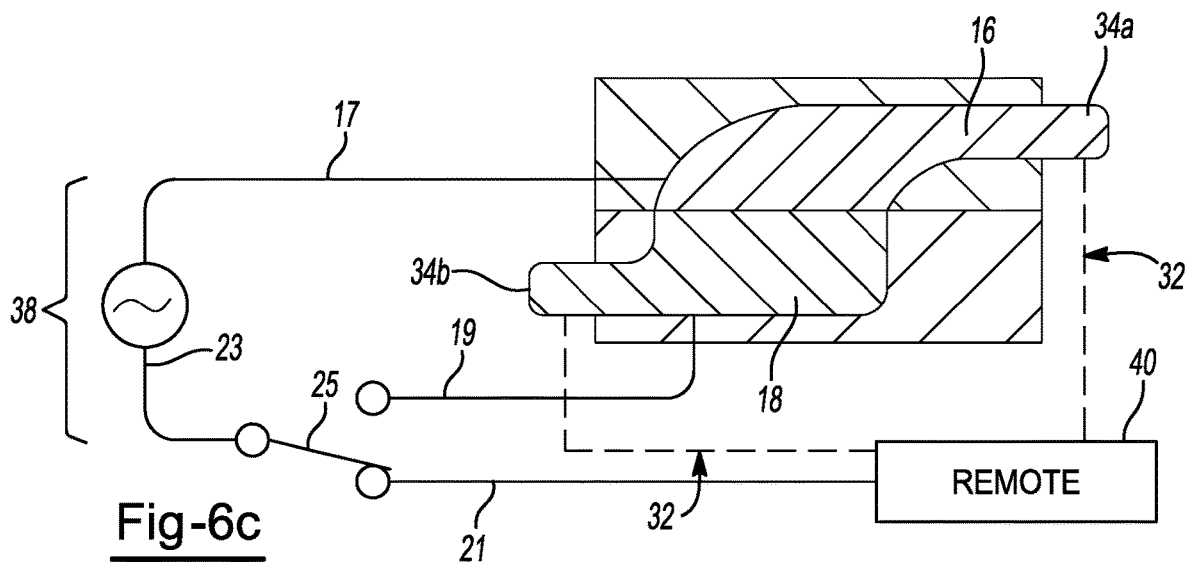
FIG. 6c shows an additional illustrative example of a tip arrangement and electrical circuit of an electrosurgical instrument in accordance with the present teachings.

FIG. 6c shows the instrument tip of FIGS. 6a and 6b in use in monopolar mode, whereby the circuit 38 no longer connects the first electrode 16 and second electrode 18. As shown, both first extension portions 34a, 34b of the first and second electrode are connected to a monopolar energy source and the energy path 32 flows through each extension portion, through tissue (not shown), to a remote ground pad 40. As shown, during use in monopolar mode, the first and second electrodes are in electrical contact with one another such that a single monopolar energy supply can provide for use of both extensions portions. Similar to the bipolar configuration shown at FIG. 6b, the first electrode is connected to the power source via the first connector 17. However the second electrode is free of any connectivity to the power source via the second connector 19. However, the connector portion 23 that was part of the second connector in bipolar mode is connected to the power source and also now connected to the third connector 21 via a connector portion 25.

Figure 7:
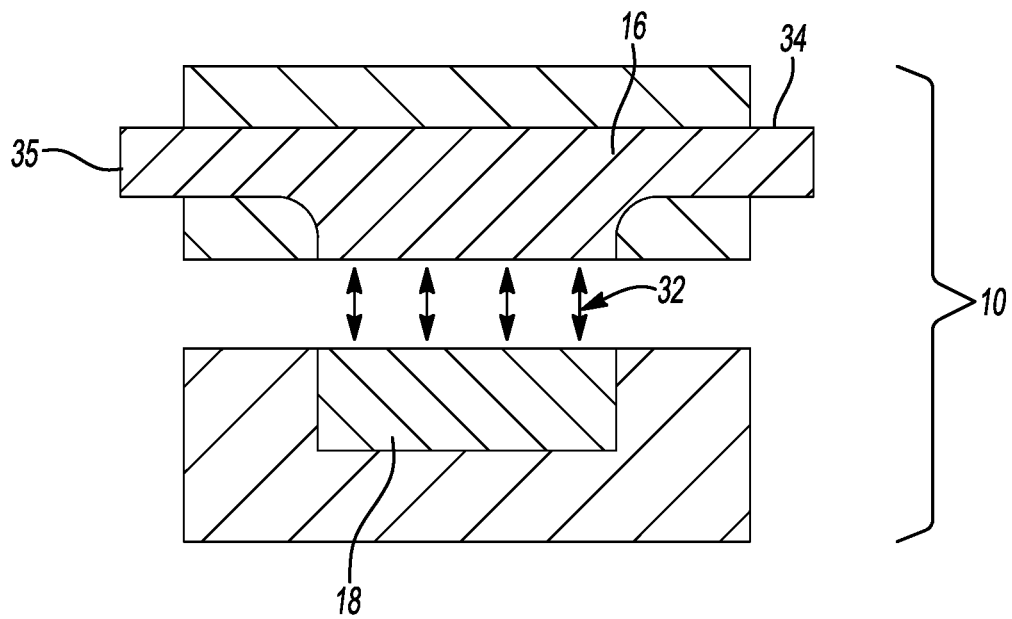
FIG. 7 shows an additional illustrative example of a tip arrangement of an electrosurgical instrument in accordance with the present teachings.

As shown for example in FIG. 7, the instrument tip 10 may include a first electrode 16 may include a first extension portion 34 and a second extension portion 35. One or both of the first and second extension portions may pass energy when in monopolar mode. The first electrode 16 may also pass energy in bipolar mode such that a bipolar energy path 32 flows between the first electrode 16 and second electrode 18.

Figure 8A:
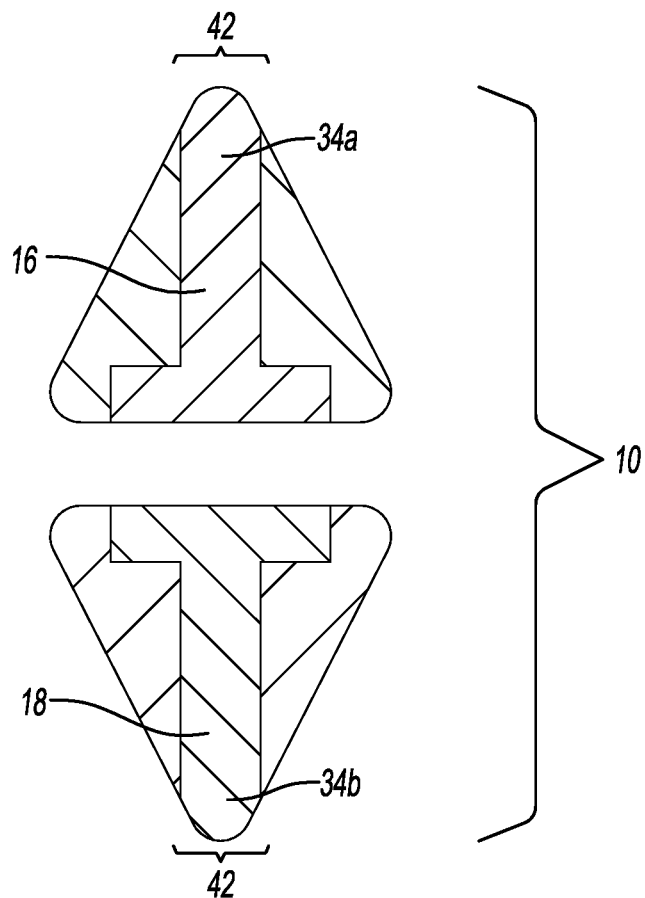
FIG. 8a shows an additional illustrative example of a tip arrangement of an electrosurgical instrument in accordance with the present teachings.
Figure 8B:
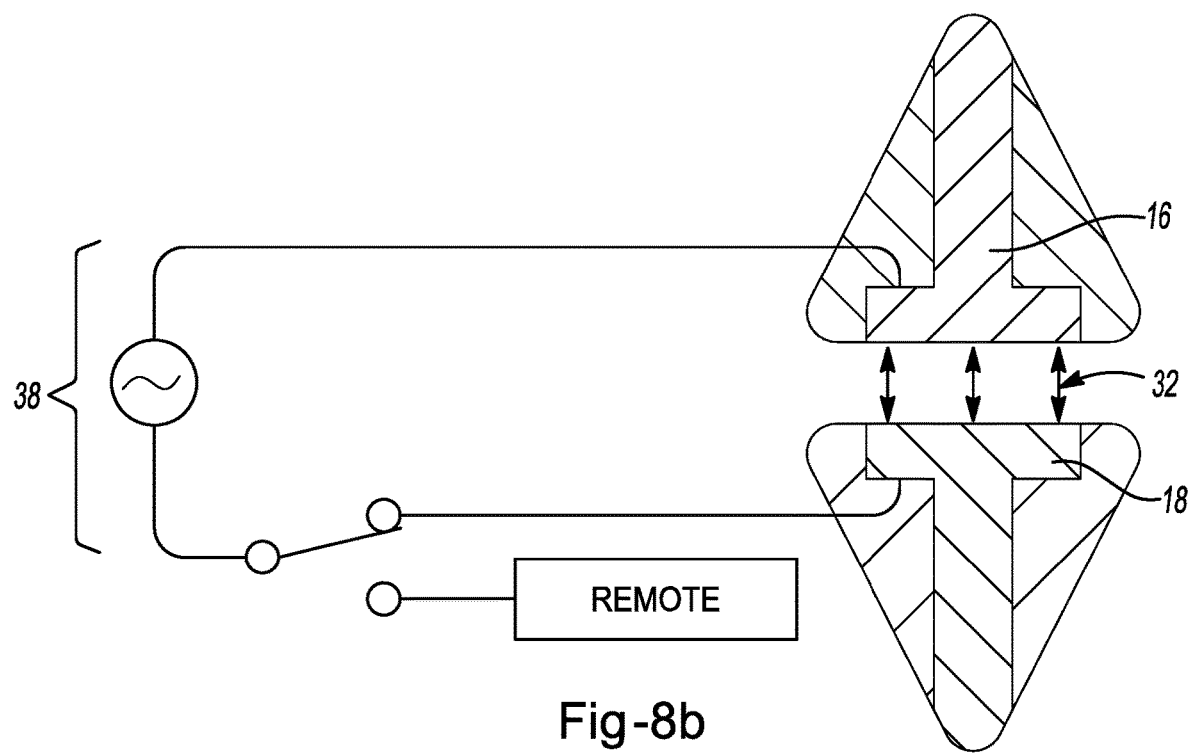
FIG. 8b shows an additional illustrative example of a tip arrangement and electrical circuit of an electrosurgical instrument in accordance with the present teachings.
Figure 8C:
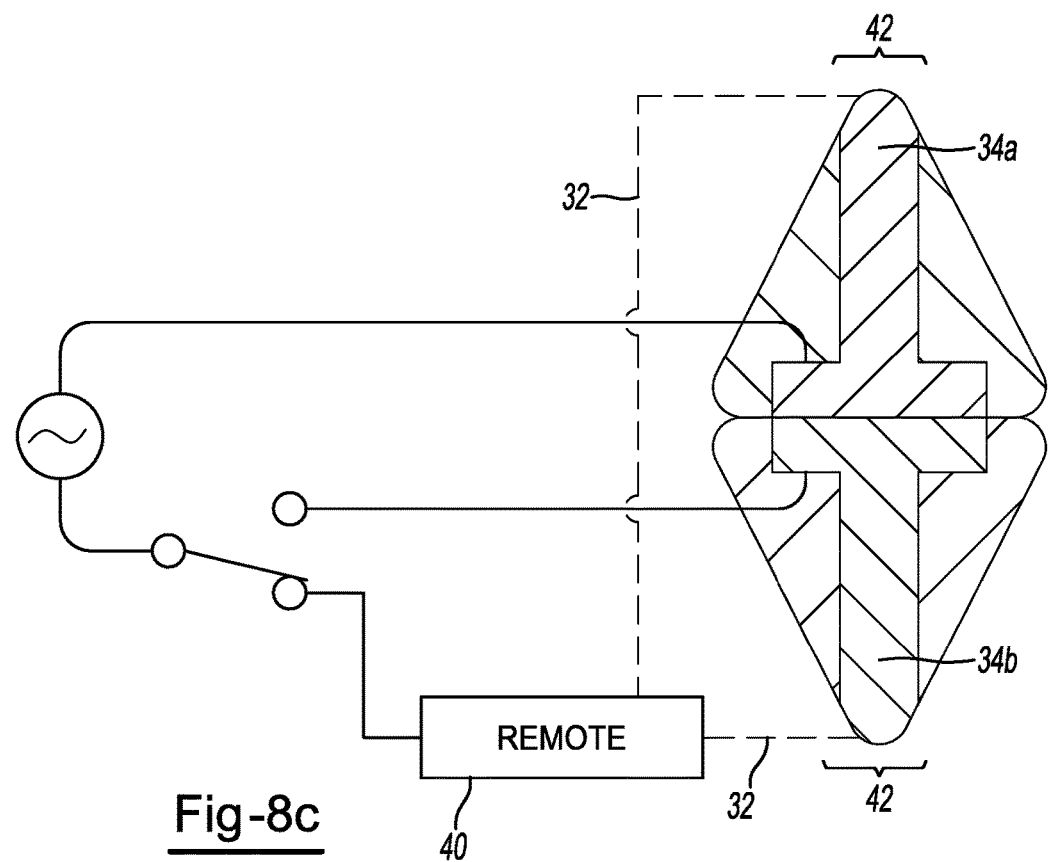
FIG. 8c shows an additional illustrative example of a tip arrangement and electrical circuit of an electrosurgical instrument in accordance with the present teachings.

A first extension portion 34a, 34b may extend from a spine portion 42 of the instrument tip 10 as shown in FIGS. 8a-8c. FIG. 8a shows an exemplary instrument tip 10 including a first electrode 16 and second electrode 18, each including a first extension portion 34a, 34b extending from a spine portion 42 of the instrument tip. FIG. 8b shows the instrument tip of FIG. 8a when in use in bipolar mode. As shown, the energy path 32 from the circuit 38 flows between the first electrode 16 and the second electrode 18. Alternatively, as shown in FIG. 8c, in monopolar mode, the energy path 32 flows from one or more of the first extension portions 34a, 34b located on the spine portion 42 through tissue (not shown) to a ground pad 40. As shown, during use in monopolar mode, the first and second electrodes are in electrical contact with one another such that a single monopolar energy supply can provide for use of both extensions portions.

Figure 9:
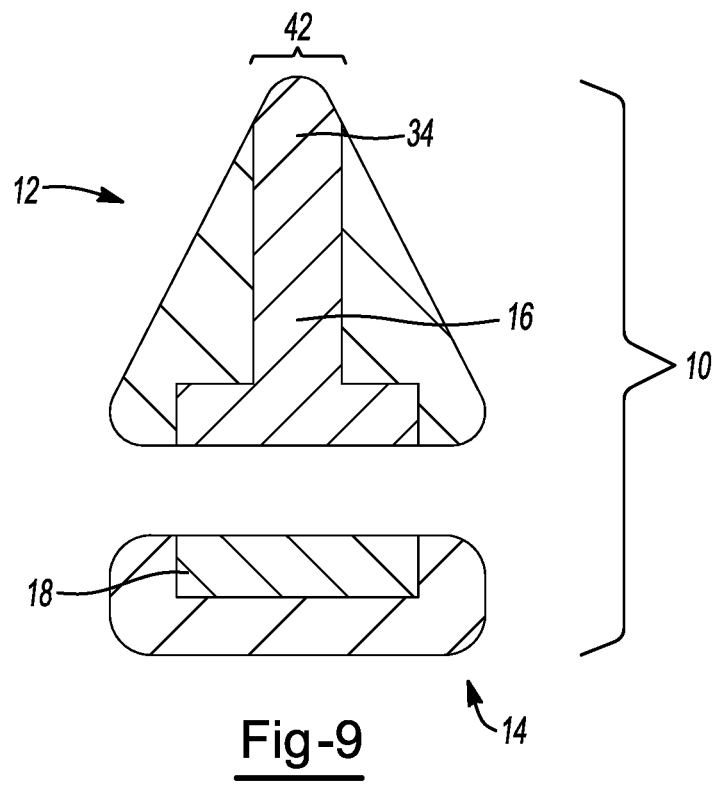
FIG. 9 shows an additional illustrative example of a tip arrangement of an electrosurgical instrument in accordance with the present teachings.

Alternatively, only one of the first or second electrode may include an extension portion that extends from a spine portion of the instrument tip. As shown for example at FIG. 9, the first electrode 16 includes an extension portion 34 extending from the spine portion 42 of the first arm 12 of the instrument tip 10. As shown the second arm 14 includes a second electrode 18, however the second electrode is free of any extension portion and thus may not be in receipt of any energy flow during use of the instrument tip in monopolar mode.

Figure 10:
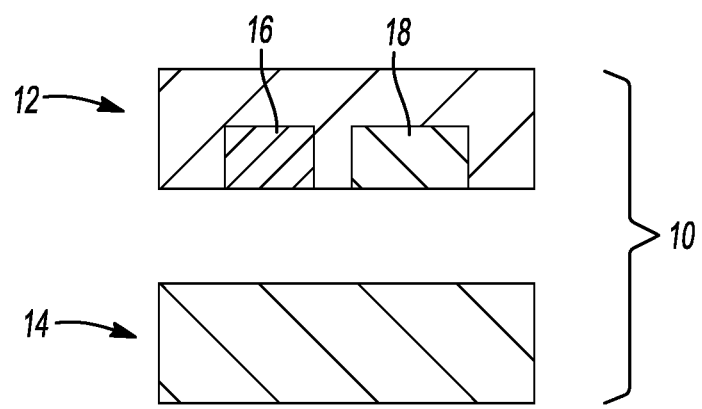
FIG. 10 shows an additional illustrative example of a tip arrangement of an electrosurgical instrument in accordance with the present teachings.

FIG. 10 depicts an alternative instrument tip arrangement wherein the first electrode 16 and second electrode 18 are both located on the first arm 12 of the instrument tip 10. The embodiment shown at FIG. 10 further includes a second arm 14 of the instrument tip that is free of any electrode. Both the first arm 12 and the second arm 14 are free of any electrode that passes energy in monopolar mode.

Figure 11A:
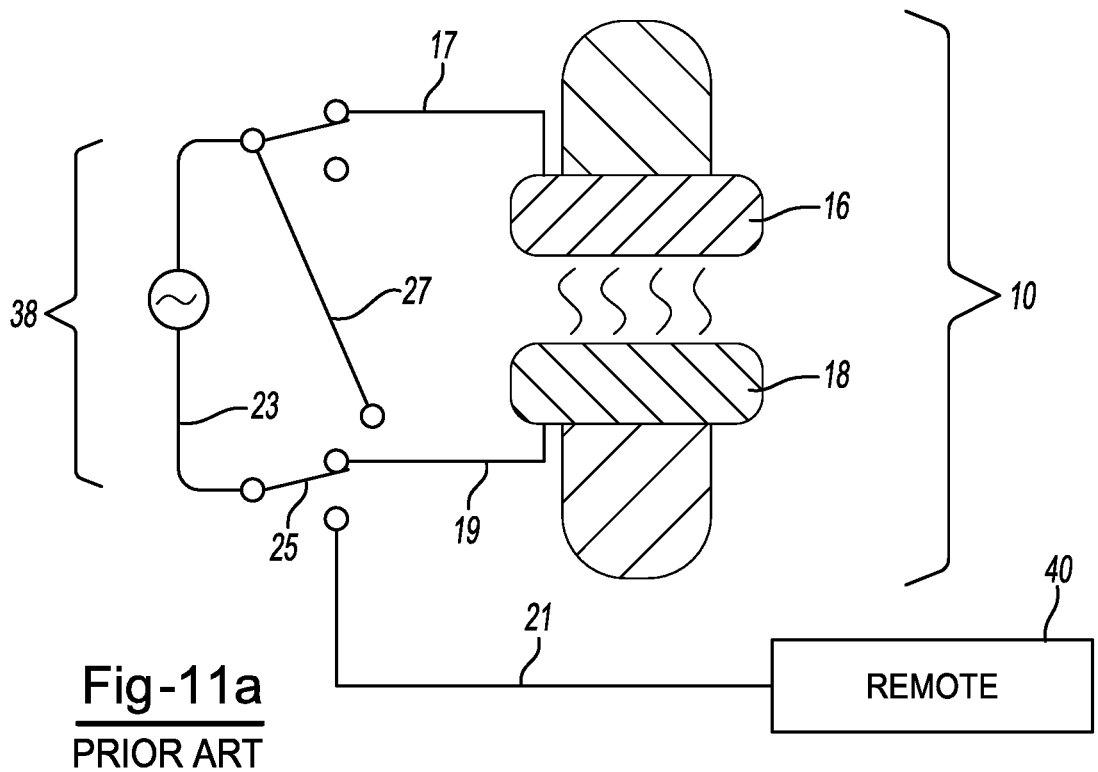
FIG. 11a shows an example of a tip arrangement and electrical circuit of an electrosurgical instrument in accordance with the teachings in the prior art.
Figure 11B:
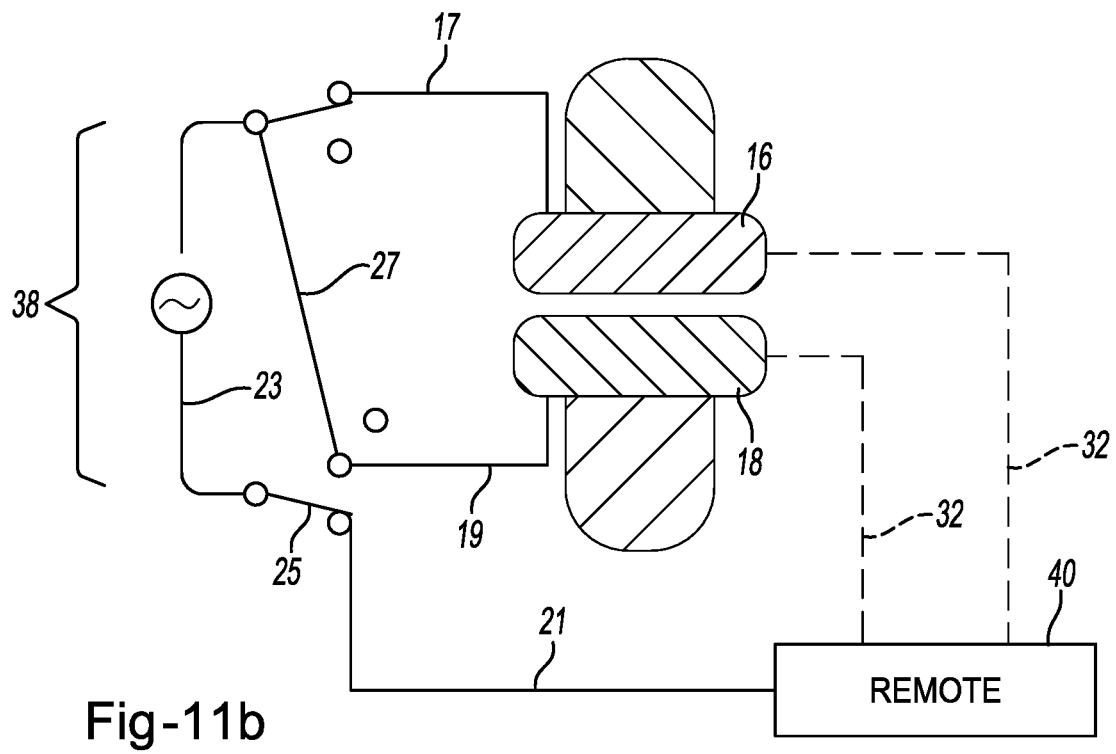
FIG. 11b shows an example of a tip arrangement and electrical circuit of an electrosurgical instrument in accordance with the teachings in the prior art.
Figure 12A:
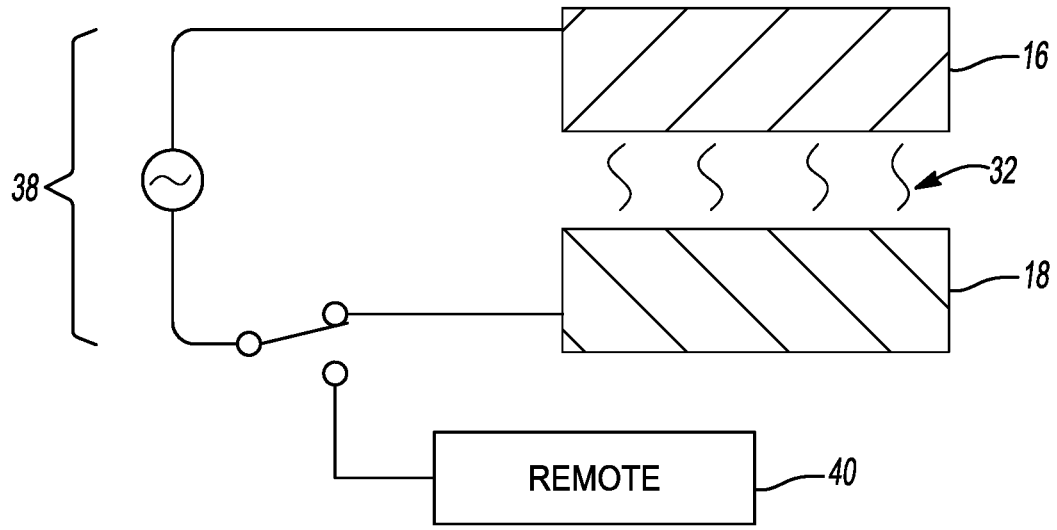
FIG. 12a shows an example of a tip arrangement and electrical circuit of an electrosurgical instrument in accordance with the teachings in the prior art.
Figure 12B:
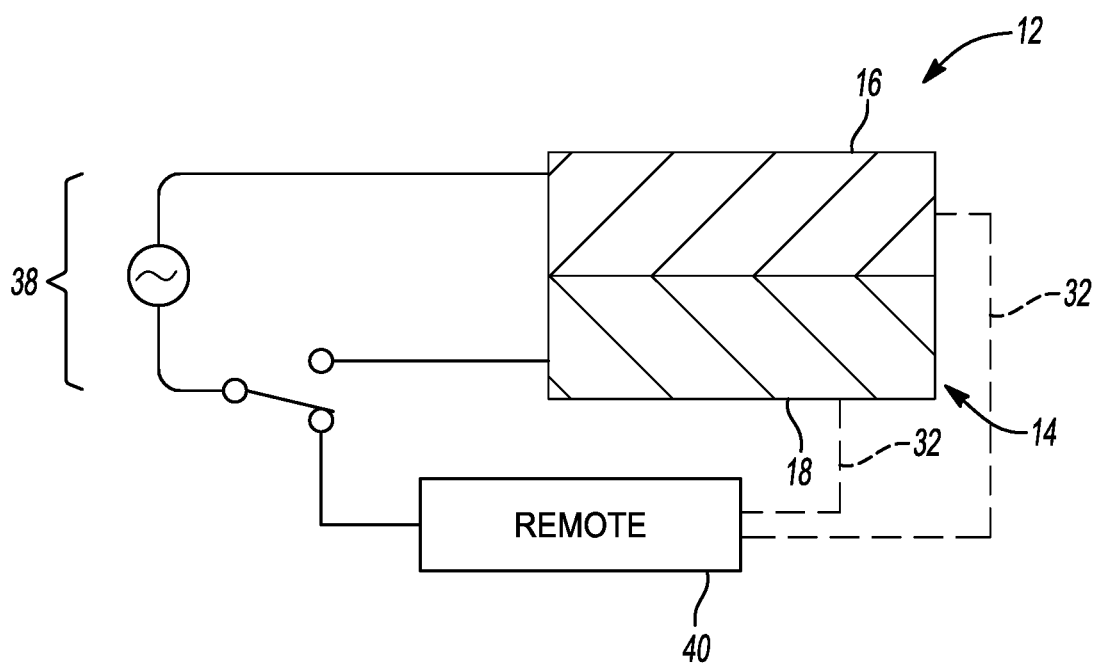
FIG. 12b shows an example of a tip arrangement and electrical circuit of an electrosurgical instrument in accordance with the teachings in the prior art.

Specific examples of prior art tip arrangements for operating in both monopolar and bipolar mode are shown at FIGS. 11a-11b and 12a-12b. As shown for example at FIG. 11a, the instrument tip 10 includes a first electrode 16 and second electrode whereby in bipolar mode the circuit 38 connects the first and second electrodes 16, 18 and remains unconnected to any ground pad 40. The first electrode 16 is connected to a power source via a first connector 17. The second electrode 18 is connected to a power source via a second connector formed of multiple connector portions 19, 23, 25. Additional connectors 21, 27 are not utilized in the circuit when in bipolar mode. However, as shown in FIG. 11b, the circuit 38 is arranged to both provide energy to the first electrode 16 and second electrode 18 and also connect via an energy path 32 to a ground pad 40 in monopolar mode. Additional connector 21 is connected to second connector 25 for forming a circuit that includes the ground pad 40. Additional connector 27 is also included in the circuit by connecting to second connector portion 19. Prior art instrument tip arrangements arranged to provide only monopolar or only bipolar functionality are shown at FIGS. 12a and 12b. As shown for example in FIG. 12a, an energy path 32 is formed between the first electrode 16 and second electrode 18 when used in bipolar mode while the circuit 38 is free of any connection to a ground pad 40. However, in monopolar mode (as shown in FIG. 12b), the first arm 12 and second arm 14 are closed toward each other allowing for use of a portion of one or more of the first electrode 16 and second electrode in monopolar mode whereby the circuit 38 no longer connects the first electrode and second electrode, but rather forms and energy path 32 that includes the ground pad 40. These prior arrangements include first and second electrodes that are free of any portion that extends from the spine portion (e.g., a back edge of the arm) or an exterior side edge of the arm. Thus, the first and second electrodes are joined to form a common monopolar electrode that is blunt and free of any extension portion (e.g., blade).

Figure 13:
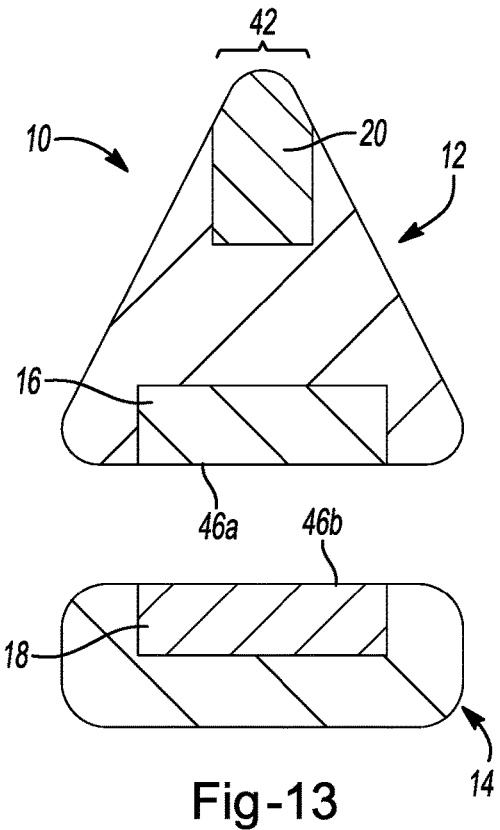
FIG. 13 shows an additional illustrative example of a tip arrangement of an electrosurgical instrument in accordance with the present teachings.
Figure 14:
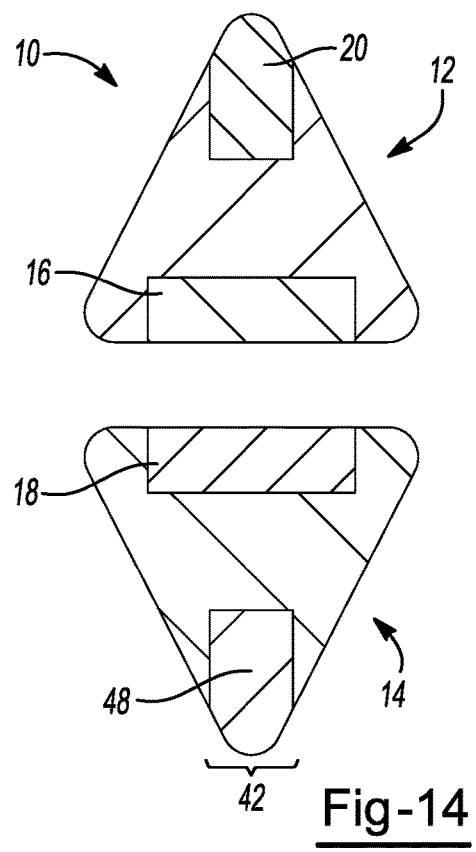
FIG. 14 shows an additional illustrative example of a tip arrangement of an electrosurgical instrument in accordance with the present teachings.
Figure 15:
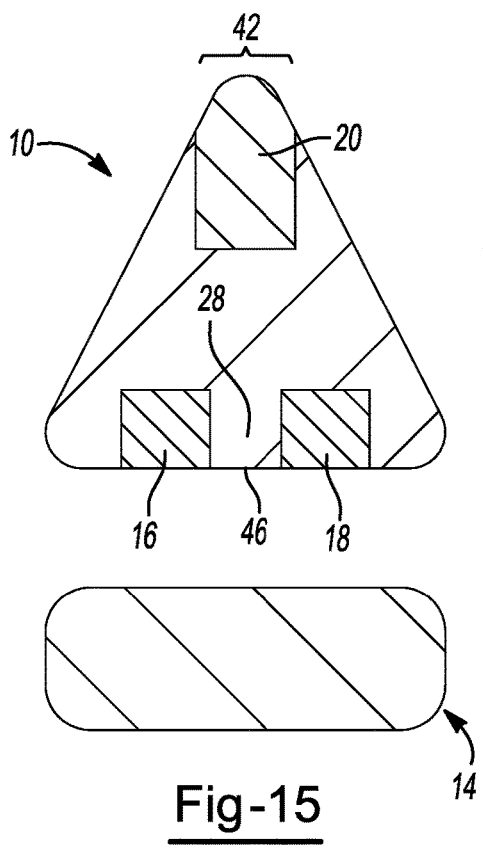
FIG. 15 shows an additional illustrative example of a tip arrangement of an electrosurgical instrument in accordance with the present teachings.

The instrument tip may be arranged to include multiple distinct electrodes on one arm whereby one electrode passes energy only in bipolar mode and one passes energy only in monopolar mode. More specifically, as shown at FIG. 13, the first arm 12 includes a first electrode 16 and the second arm 14 includes the second electrode 18. The first arm further includes a third electrode 20 whereby the third electrode is free of any direct connection with the first electrode 16. The third electrode 20 is located along a spine portion 42 of the instrument tip 10 whereas the first electrode and second electrode are located along an inner surface portion 46a, 46b of each of the first arm and second arm. FIG. 14 depicts a similar instrument tip arrangement where both the first arm 12 and second arm 14 include multiple electrodes. Specifically, the second arm 14 includes a fourth electrode 48 located along a spine portion 42 of the instrument tip 10, similar in location to the third electrode 20 on the first arm 12. In a similar configuration, electrodes 20 and 48 are electrically connected via one or more wires (not shown). Thus electrodes 20 and 48 would act as a common monopolar electrode to produce a two sided scalpel, similar to that depicted in FIG. 8c. FIG. 15 depicts yet another instrument tip embodiment including more than two electrodes. The first arm 12 includes a first and second electrode 16, 18 located along the inner surface portion 46 of the instrument tip, separated by an insulation portion 28. The first arm also includes a third electrode 20 located along a spine portion 42 of the instrument tip. The first and second electrodes thus pass energy in bipolar mode whereas the third electrode 20 passes energy in monopolar mode. The second arm 14 is free of any conductive element.

Figure 16:
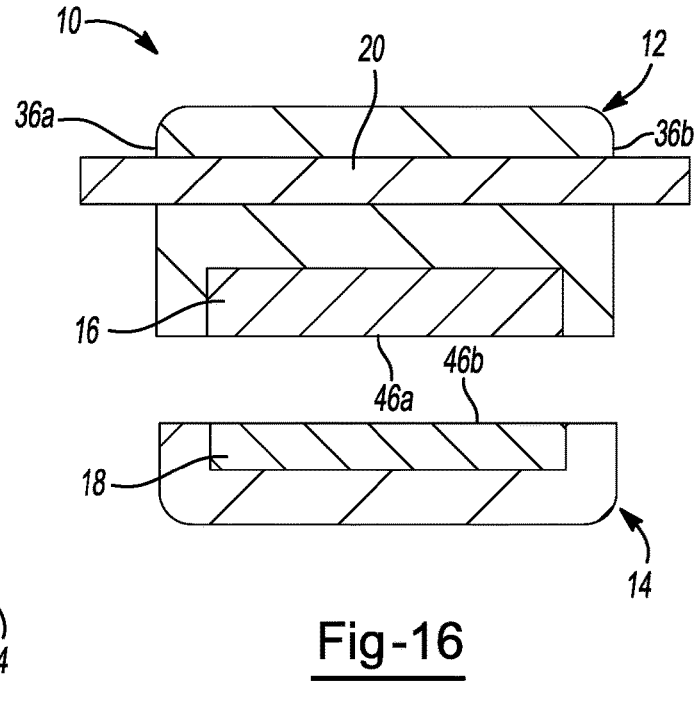
FIG. 16 shows an additional illustrative example of a tip arrangement of an electrosurgical instrument in accordance with the present teachings.
Figure 17:
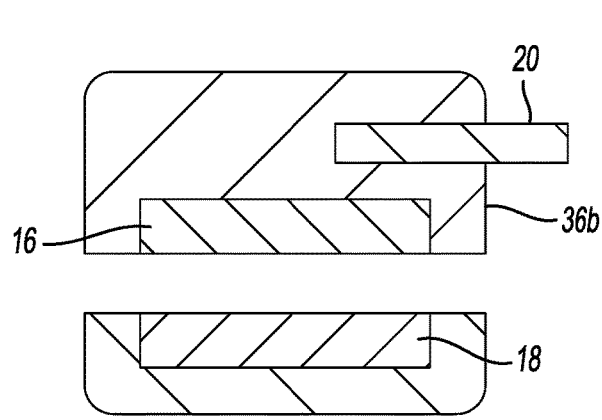
FIG. 17 shows an additional illustrative example of a tip arrangement of an electrosurgical instrument in accordance with the present teachings.

FIG. 16 shows an instrument tip arrangement similar to that of FIG. 13. The first arm 12 includes a first electrode 16 and the second arm 14 includes the second electrode 18. The first arm further includes a third electrode 20 whereby the third electrode is free of any direct connection with the first electrode 16. The third electrode 20 is located so that it extends from both opposing terminating side edges 36a, 36b of the first arm 12 of instrument tip 10 to produce a two sided scalpel, whereas the first electrode and second electrode are located along an inner surface portion 46a, 46b of each of the first arm and second arm. FIG. 17 depicts an instrument tip arrangement similar to that of FIG. 16, however only the third electrode 20 extends from only one terminating side edge 36b of the first arm to produce a one sided scalpel.

Figure 18:
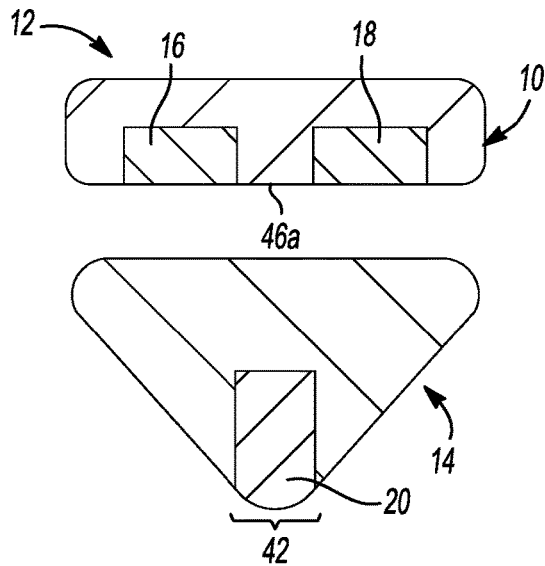
FIG. 18 shows an additional illustrative example of a tip arrangement of an electrosurgical instrument in accordance with the present teachings.

FIG. 18 shows another embodiment similar to FIG. 15 where the first electrode 16 and second electrode 18 are located along the inner surface portion 46a of the first arm 12. However, the second arm includes a third electrode 20 located along the spine portion 42 of the instrument tip.

Figure 19:
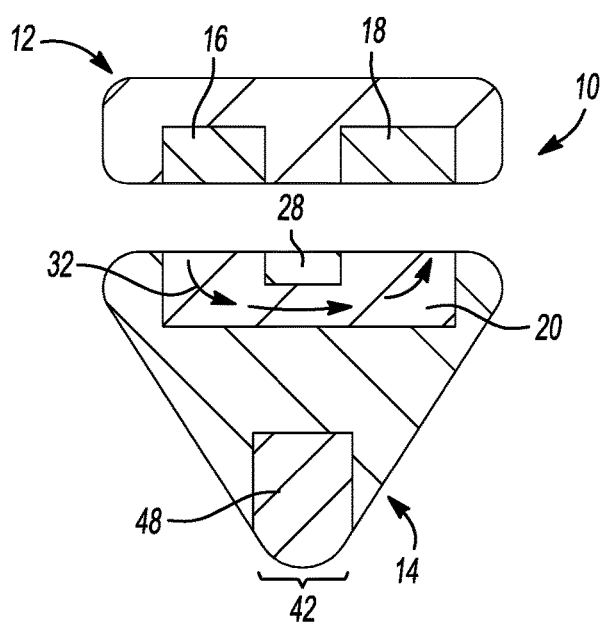
FIG. 19 shows an additional illustrative example of a tip arrangement of an electrosurgical instrument in accordance with the present teachings.
Figure 20:
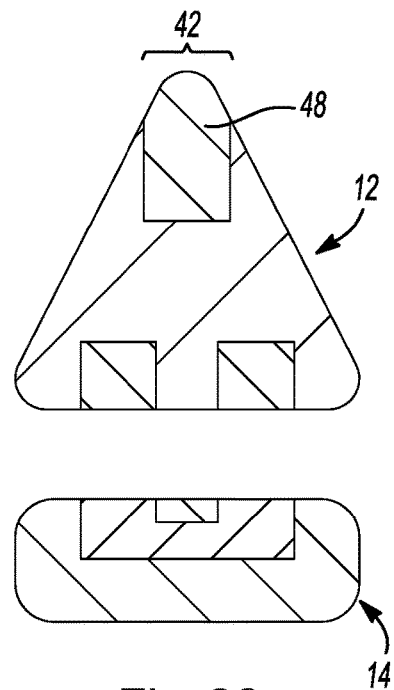
FIG. 20 shows an additional illustrative example of a tip arrangement of an electrosurgical instrument in accordance with the present teachings.
Figure 21A:
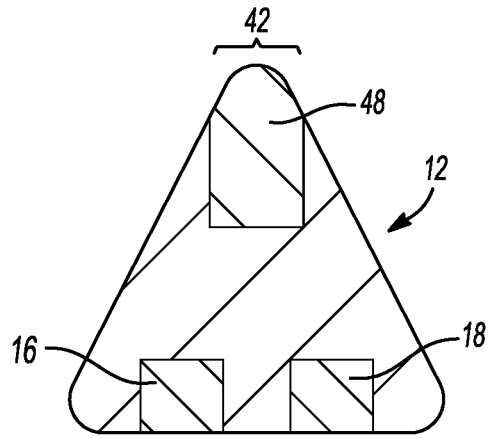
FIG. 21a shows an additional illustrative example of a tip arrangement of an electrosurgical instrument in accordance with the present teachings.
Figure 21A:
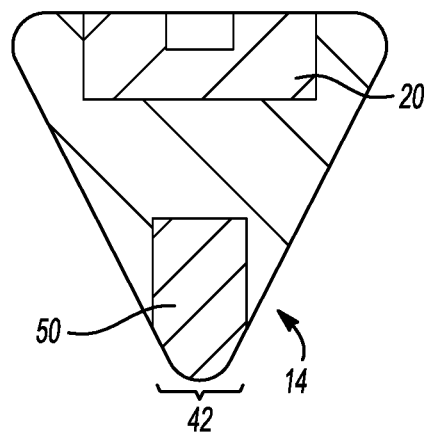
Figure 21B:
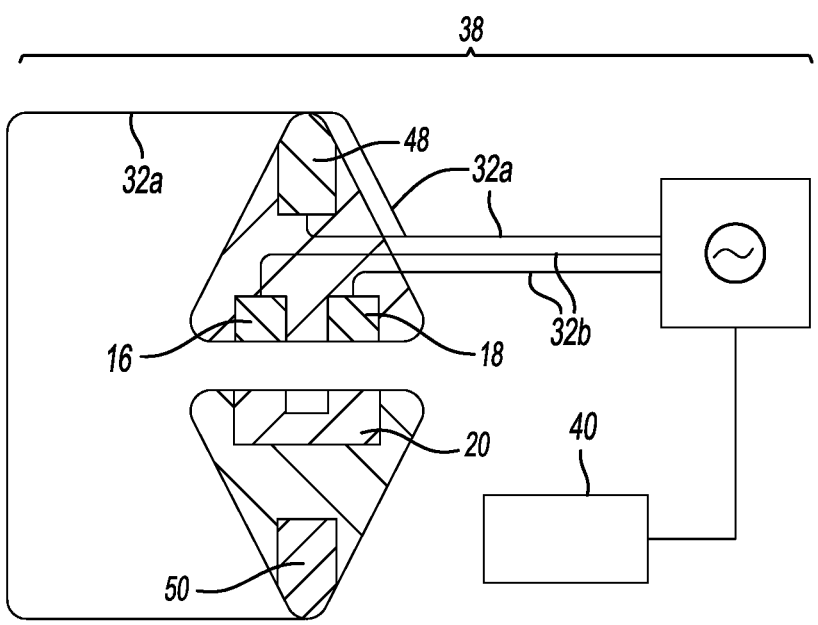
FIG. 21b shows an additional illustrative example of a tip arrangement and electrical circuit of an electrosurgical instrument in accordance with the present teachings.

FIG. 19 shows an instrument tip arrangement including a first electrode 16 and second electrode 18 on first arm 12. The instrument tip 10 further includes a third electrode 20 (e.g., a conductive element) on the second arm 14 opposing the first and second electrode. A fourth electrode 48 is also included, being located along the spine portion 42 and utilized during use in monopolar mode. One or more insulation portions 28 may be included to assist in directing the energy path 32 during use of the instrument in bipolar mode. FIG. 20 depicts a similar arrangement to the instrument tip of FIG. 19, however the fourth electrode 48 is located on the spine portion 42 on the first arm 12. FIG. 21a is a combination of both FIGS. 19 and 20 whereby both the first arm 12 and second arm 14 include an electrode (e.g., a fourth electrode 48 and fifth electrode 50) on each spine portion 42 of the instrument tip 10. In a similar configuration, electrodes 20 and 48 are electrically connected via one or more wires (not shown). Thus electrodes 20 and 48 would act as a common monopolar electrode. FIG. 21b depicts the circuit connectivity of the tip arrangement of 21a. Two monopolar connector leads 32a are shown, one originating from each of the two monopolar electrodes 48, 50. Two bipolar connector leads 32b connect the power source to each of the first electrode 16 and second electrode 18.

One or more of the electrodes may be formed from more than one material. In one such embodiment, one or more of the electrodes may be formed from two discrete adjacent conductors including a thermal joint therebetween. As shown for example in FIG. 22a, the first electrode 16 is located on the first arm 12 and is formed from a first conductor 52 and a second adjacent conductor 54, thus forming a thermal joint 56 in between the two bonded conductors. The second conductor extends from the spine portion 42 of the instrument tip. The second arm 14 includes a second electrode 18 located along the inner surface 46 of the second arm. Thus the first conductor facilitates energy passage in bipolar mode while the second conductor facilitates energy passage in monopolar mode. FIG. 22b depicts the circuit connectivity of the tip arrangement of 22a. One monopolar connector lead 32a is shown originating from the monopolar electrode 54. Two bipolar connector leads 32b connect the power source to each of the first electrode 16 and second electrode 18.

Figure 23:
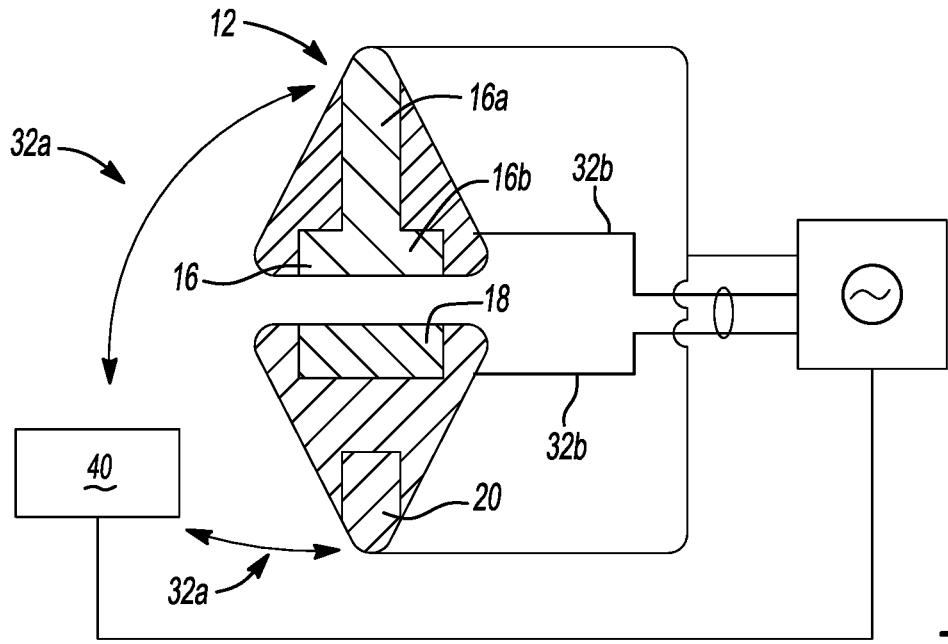
FIG. 23 shows an additional illustrative example of a tip arrangement of an electrosurgical instrument in accordance with the present teachings.

FIG. 23 depicts a three electrode system where the first arm 12 includes a first electrode 16 and the second arm includes a second electrode 18 and a third electrode 20. A portion 16a of the first electrode is utilized when the device is in monopolar mode and a second portion 16b of the first electrode is utilized when the device is in bipolar mode. The energy path 32a in monopolar mode extends from each electrode or electrode portion 16a, 20 utilized for monopolar activity to the ground pad 40. The bipolar leads 32b extend from a power source to the electrodes or electrode portions 16b, 18 utilized when the device in bipolar mode.

Figure 22A:
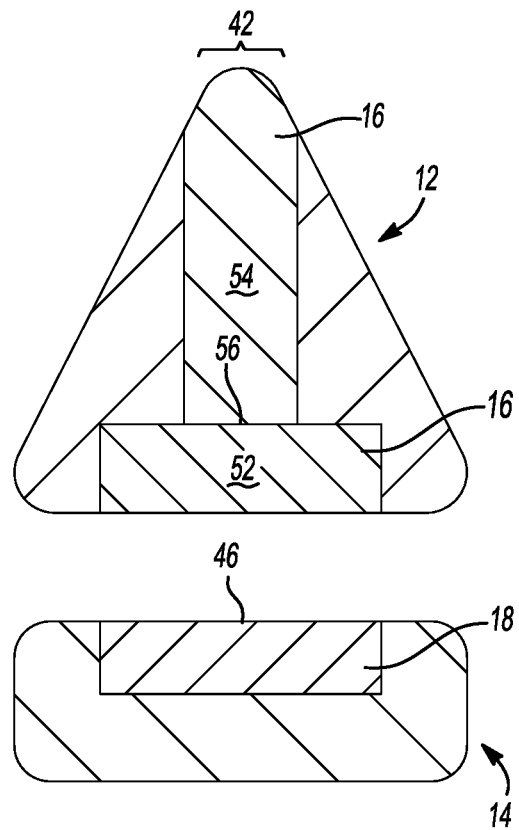
FIG. 22a shows an additional illustrative example of a tip arrangement of an electrosurgical instrument in accordance with the present teachings.
Figure 22B:
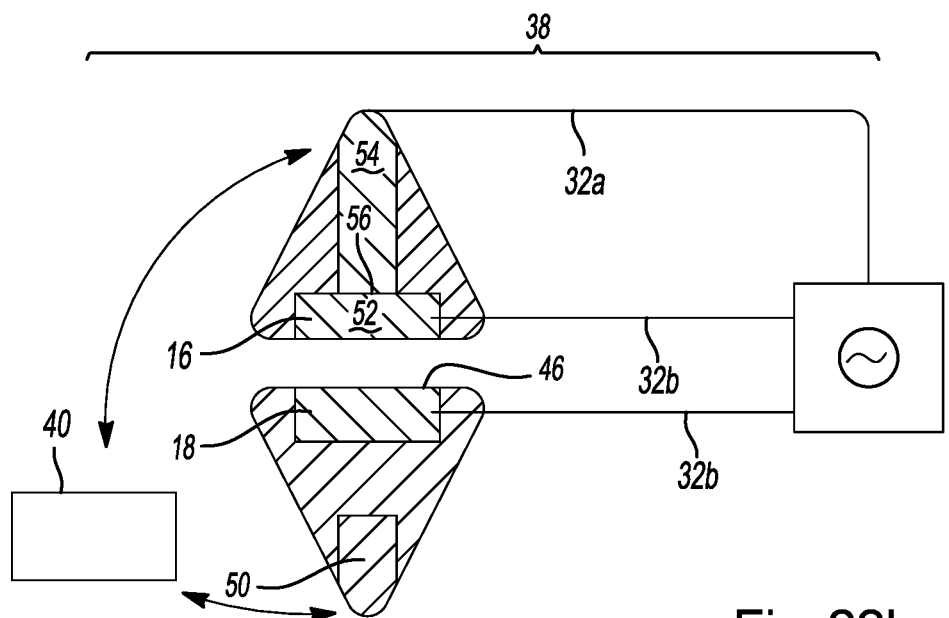
FIG. 22b shows an additional illustrative example of a tip arrangement and electrical circuit of an electrosurgical instrument in accordance with the present teachings.
Figure 24:
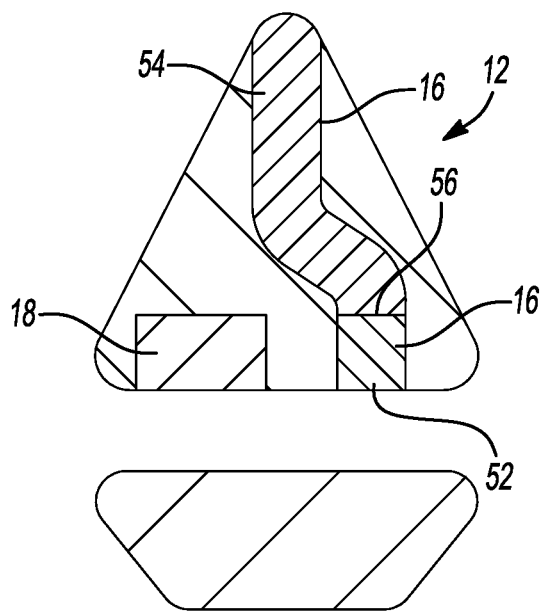
FIG. 24 shows an additional illustrative example of a tip arrangement of an electrosurgical instrument in accordance with the present teachings.
Figure 25:
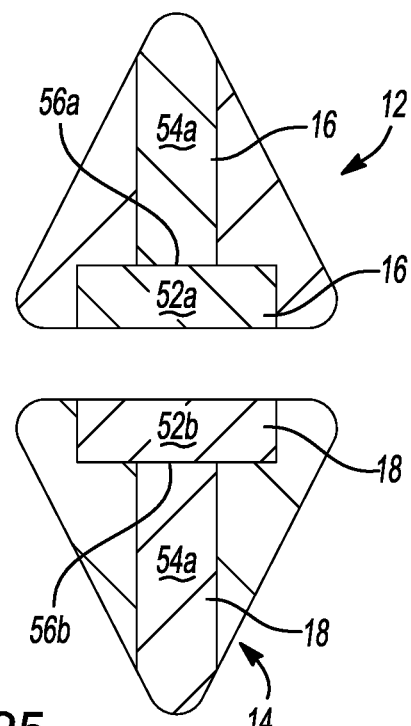
FIG. 25 shows an additional illustrative example of a tip arrangement of an electrosurgical instrument in accordance with the present teachings.
Figure 26:
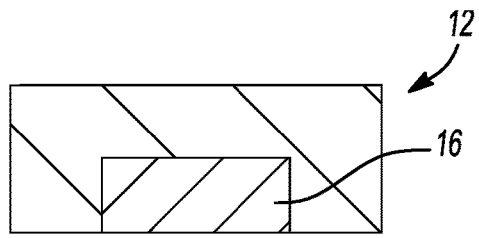
FIG. 26 shows an additional illustrative example of a tip arrangement of an electrosurgical instrument in accordance with the present teachings.
Figure 26:
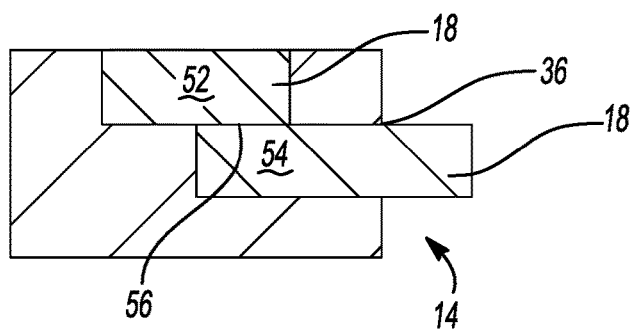

FIG. 24 shows a similar embodiment to that of FIGS. 22a and 22b, however in addition to the first arm 12 including a first electrode 16 being formed of multiple distinct conductors 52, 54, the first arm also includes a second standard electrode 18. FIG. 25 shows yet another alternative embodiment including both of the first arm 12 and second arm 14 including an electrode formed of a first and second conductor 52a, 52b, 54a, 54b having a thermal joint 56a, 56b therebetween (e.g., the first electrode 16 and second electrode 18 are each formed of multiple adjacent distinct conductors). FIG. 26 shows an embodiment similar to that of FIGS. 22a-22b whereby one electrode (in the case the second electrode 18) is formed of multiple distinct conductors. As shown, the first arm 12 includes a first electrode 16 and the second arm 14 includes a second electrode 18, whereby the second electrode is formed of a first conductor 52 bonded to a second conductor 54 connected by a thermal joint 56. However, unlike FIGS. 22a-22b, the embodiment of FIG. 26 includes an instrument tip arrangement where the second conductor 54 extends from an exterior side edge 36 of the second arm 14.

Figure 27A:
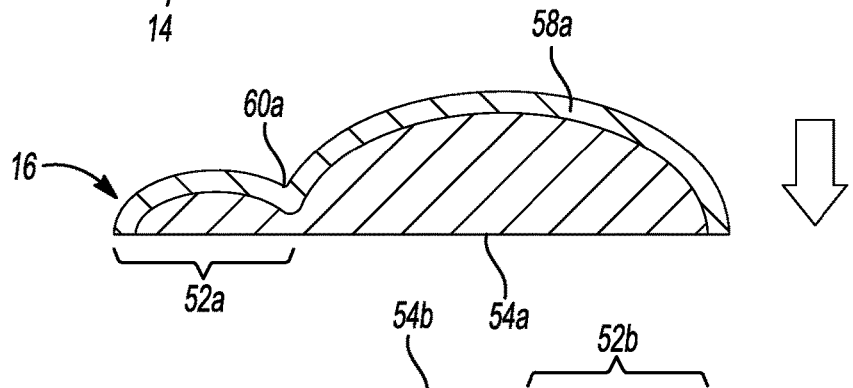
FIG. 27a shows an additional illustrative example of a tip arrangement of an electrosurgical instrument in accordance with the present teachings.
Figure 27B:
FIG. 27b shows an additional illustrative example of a tip arrangement of an electrosurgical instrument in accordance with the present teachings.
Figure 27B:
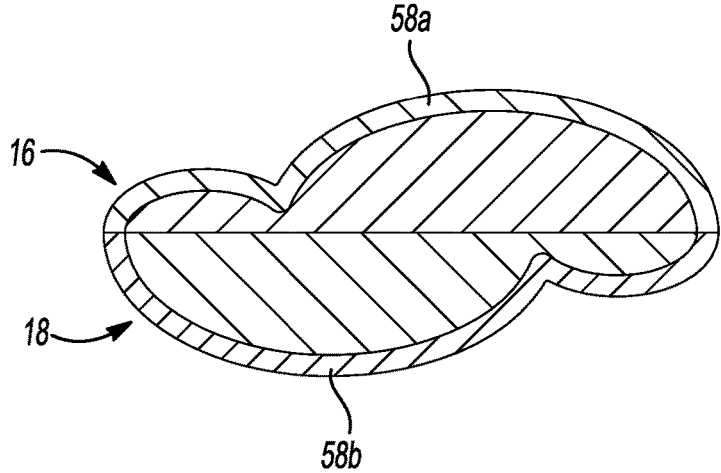

FIGS. 27a and 27b depict a further embodiment whereby the shape of the conductor material creates a thermal joint configuration. Each of the first and second electrode 16, 18 are formed of a bottle-neck conductor 58a, 58b. Each bottle neck conductor includes a first conductor portion (e.g., lobes) 52a, 52b and a second conductor portion (e.g., lobes) 54a, 54b and an indented portion 60a, 60b in between the first and second conductor portions. FIG. 26a shows the opposing conductors when the first arm and second arm are in an open position. FIG. 26b shows the conductors in a closed position.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. An electrosurgical instrument comprising forceps having:
 a first arm including an inner tissue-engaging surface, an outer spine surface, a plurality of side surfaces extending between the inner tissue-engaging surface and the outer spine surface, a first electrode located on the inner tissue-engaging surface, and a first electrode extension portion extending from the first electrode to the outer spine surface, the first electrode and the first electrode extension portion together forming a T-shaped electrode in the first arm; and
 a second arm opposing the first arm, the second arm including an inner tissue-engaging surface that faces the inner tissue-engaging surface of the first arm, an outer surface, a plurality of side surfaces extending between the inner-tissue engaging surface and the outer surface, and a second electrode located on the inner tissue-engaging surface;
 wherein the first electrode extension portion passes energy in a monopolar mode from the outer spine surface of the first arm when the first arm and the second arm are in a fully closed position and the first and second electrodes are in electrical contact with one another, and the first and second electrodes pass energy in a bipolar mode from the inner tissue-engaging surfaces of the first and second arms, respectively, when the first arm and the second arm are in a partially closed position with tissue grasped therebetween.

2. The electrosurgical instrument of claim 1, wherein the second arm carries an insulation portion.

3. The electrosurgical instrument of claim 1, wherein the first arm includes exactly two electrodes.

4. The electrosurgical instrument of claim 1, wherein the first arm includes exactly one electrode that passes energy in monopolar mode.

5. The electrosurgical instrument of claim 4, wherein the exactly one electrode of the first arm is the only monopolar electrode that is electrically connected to an energy source.

6. The electrosurgical instrument of claim 1, wherein the first arm defines a generally triangular cross-sectional shape.

7. The electrosurgical instrument of claim 6, wherein the first electrode defines a planar electrode face along the tissue-engaging surface of the first arm, and wherein the first electrode extension portion defines a curved electrode face along the outer spine surface of the first arm.

8. An electrosurgical instrument comprising forceps having:
 a first arm defining a generally triangular cross-sectional shape and including an inner tissue-engaging surface defining a first width, an outer spine surface facing away from the inner tissue-engaging surface and defining a smaller second width, a plurality of converging side surfaces joining the inner tissue-engaging surface and the outer spine surface, a first electrode located on the inner tissue-engaging surface, a first electrode extension portion extending from the first electrode to the outer spine surface, and a second electrode located on the inner tissue-engaging surface, wherein the first electrode defines a first surface area along the inner tissue-engaging surface and the first electrode extension portion defines a second smaller surface area along the outer spine surface; and
 a second arm opposing the first arm, the second arm including an inner tissue-engaging surface that faces the inner tissue-engaging surface of the first arm, an outer surface, a plurality of side surfaces extending between the inner-tissue engaging surface and the outer surface, and a conductive element located on the inner tissue-engaging surface;
 wherein the conductive element is a floating electrode so that a preferential path is created for energy flow from one or more of the first and second electrodes via the floating electrode in bipolar mode; and
 wherein the first electrode extension portion passes energy in a monopolar mode from the outer spine surface of the first arm and the one or more of the first and second electrodes and the conductive element pass energy in a bipolar mode from the inner tissue-engaging surfaces of the first and second arms, respectively.

9. The electrosurgical instrument of claim 8, wherein the second arm carries an insulation portion.

10. The electrosurgical instrument of claim 8, wherein the second arm includes an insulation portion that opposes an insulation portion between the first and second electrodes.

11. The electrosurgical instrument of claim 8, wherein the second arm includes an insulation portion located on an inner surface of the second arm so that bipolar energy travels through a larger portion of the tissue as compared to that of a second arm without the insulation portion.

12. The electrosurgical instrument of claim 8, wherein the first arm includes exactly two electrodes.

13. The electrosurgical instrument of claim 8, wherein the first arm includes exactly one electrode that passes energy in monopolar mode.

14. The electrosurgical instrument of claim 13, wherein the exactly one electrode of the first arm is the only monopolar electrode that is electrically connected to an energy source.

15. An electrosurgical instrument comprising:
 a first arm including an inner tissue-engaging surface, an outer spine surface oriented away from the tissue-engaging surface, a plurality of side surfaces extending between the inner tissue-engaging surface and the outer spine surface, a first electrode located on the inner tissue-engaging surface, a second electrode located on the inner tissue-engaging surface, and a second electrode extension portion extending from the second electrode to the outer spine surface, the second electrode and the second electrode extension portion together forming a T-shaped electrode in the first arm; and
 a second arm opposing the first arm and including an inner tissue-engaging surface;
 wherein the second electrode is formed from a first conductor, the second electrode extension portion is formed from a second adjacent conductor, and the first and second conductors are bonded together such that a thermal joint is formed therebetween; and
 wherein the second electrode extension portion passes energy in a monopolar mode from the outer spine surface of the first arm and the first electrode and second electrode pass energy in a bipolar mode from the inner tissue-engaging surface of the first arm.

16. The electrosurgical instrument of claim 15, wherein the second arm carries an insulation portion.

17. The electrosurgical instrument of claim 15, wherein the second arm includes an insulation portion that opposes an insulation portion between the first and second electrodes.

18. The electrosurgical instrument of claim 15, wherein the second arm includes a conductive element and an insulation portion located on an inner surface of the second arm so that bipolar energy travels through a larger portion of the tissue as compared to that of a second arm without the insulation portion.

19. The electrosurgical instrument of claim 15, wherein the first arm includes exactly two electrodes.

20. The electrosurgical instrument of claim 15, wherein the first arm includes exactly one electrode that passes energy in monopolar mode.

21. The electrosurgical instrument of claim 20, wherein the exactly one electrode of the first arm is the only monopolar electrode that is electrically connected to an energy source.

22. The electrosurgical instrument of claim 15, wherein the second arm includes a third electrode.

\* \* \* \* \*